(12) United States Patent
Naito et al.

(10) Patent No.: US 9,618,788 B2
(45) Date of Patent: Apr. 11, 2017

(54) OPTICAL FILM, POLARIZING PLATE AND LIQUID CRYSTAL DISPLAY USING THE SAME

(71) Applicant: FUJIFILM Corporation, Tokyo (JP)

(72) Inventors: Yu Naito, Kanagawa (JP); Nobutaka Fukagawa, Kanagawa (JP); Aiko Yoshida, Kanagawa (JP); Hideyuki Nishikawa, Kanagawa (JP); Masaki Noro, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 140 days.

(21) Appl. No.: 14/633,883

(22) Filed: Feb. 27, 2015

(65) Prior Publication Data

US 2015/0253621 A1    Sep. 10, 2015

(30) Foreign Application Priority Data

Mar. 5, 2014   (JP) .................................. 2014-043366

(51) Int. Cl.
```
C09K 19/00      (2006.01)
G02F 1/1335     (2006.01)
C07D 251/30     (2006.01)
```
(52) U.S. Cl.
CPC ..... *G02F 1/133528* (2013.01); *C07D 251/30* (2013.01); *Y10T 428/10* (2015.01); *Y10T 428/1036* (2015.01); *Y10T 428/1041* (2015.01)

(58) Field of Classification Search
CPC ... G02F 1/133528; C07D 251/30; C08L 1/10; C08L 1/12; C08L 1/14; Y10T 428/10;

(Continued)

(56) References Cited

U.S. PATENT DOCUMENTS

| 3,690,884 A * | 9/1972 | Scheibitz et al. | ........ G03C 5/56 430/141 |
| 2011/0134374 A1* | 6/2011 | Fukagawa | .................. C08J 5/18 349/96 |

FOREIGN PATENT DOCUMENTS

| JP | H07-333780 A | 12/1995 |
| JP | 08-062767 A | 3/1996 |

(Continued)

OTHER PUBLICATIONS

Notification of Reasons for Refusal issued by the Japanese Patent Office on Oct. 25, 2016, in connection with Japanese Patent Application No. 2014-043366.

*Primary Examiner* — Ruiyun Zhang

(74) *Attorney, Agent, or Firm* — Jean C. Edwards, Esq.; Edwards Neils LLC

(57) ABSTRACT

An optical film, containing a cellulose acylate, and at least one compound represented by any of formulas (I) to (III):

Formula (I)

(Continued)

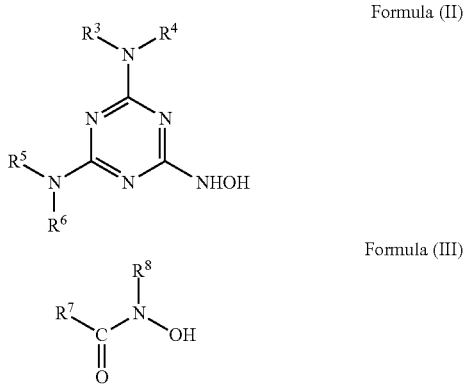

Formula (II)

Formula (III)

wherein, in formulas (I) to (III), $R^1$ and $R^2$ each independently represent a halogen atom, an alkyl, cycloalkyl, alkenyl, aryl, hydroxy, hydroxyamino, amino, alkylamino, arylamino, alkoxy, aryloxy, alkylthio, or arylthio group (however, $R^1$ and $R^2$ do not represent an amino, alkylamino, or arylamino group at the same time); $R^3$ to $R^6$ each independently represent a hydrogen atom, an alkyl, cycloalkyl, alkenyl, aryl, acyl, alkyl- or aryl-sulfonyl, alkyl- or aryl-sulfinyl, carbamoyl, sulfamoyl, alkoxycarbonyl, or aryloxycarbonyl group; $R^7$ represents an alkyl, cycloalkyl, alkenyl, aryl, alkylamino, arylamino, alkoxy, aryloxy, or heterocyclic group; $R^8$ represents an alkyl, cycloalkyl, alkenyl, aryl, or heterocyclic group; and $R^1$ to $R^8$ each may be further substituted with a substituent; and a polarizing plate and a liquid crystal display.

7 Claims, 2 Drawing Sheets

(58) Field of Classification Search
CPC ......... Y10T 428/1036; Y10T 428/1041; Y10T 428/105; C09D 101/10; C09D 101/12; C09D 101/14; C08J 2301/10; C08J 2301/12; C08J 2301/14
USPC ........ 428/1.1, 1.3, 1.31, 1.33, 220; 544/299; 349/96, 158; 106/170.1
See application file for complete search history.

(56) References Cited

FOREIGN PATENT DOCUMENTS

| | | |
|---|---|---|
| JP | 2011-053493 A | 3/2011 |
| JP | 2011-118135 A | 6/2011 |
| JP | 2011-126968 A | 6/2011 |

* cited by examiner

US 9,618,788 B2

OPTICAL FILM, POLARIZING PLATE AND LIQUID CRYSTAL DISPLAY USING THE SAME

CROSS-REFERENCE TO RELATED APPLICATION

This non-provisional application claims priority under 35 U.S.C. §119(a) on Patent Application No. 2014-043366 filed in Japan on Mar. 5, 2014, which is entirely herein incorporated by reference.

TECHNICAL FIELD

The present invention relates to an optical film, a polarizing plate and a liquid crystal display using the same.

BACKGROUND ART

Optical films, such as cellulose acylate films, are used for various liquid crystal displays, as optical elements of liquid crystal displays, for example, supports for optical compensation films, and protective films for polarizing plates.

In addition to an indoor use of the liquid crystal display, such as a TV use, a chance of the outdoor use thereof is increased, for example, use as a mobile device. As a result, development of a liquid crystal display is required, which is impervious to the use under the conditions of higher temperature and higher humidity than ever before.

Further, a demand for the liquid crystal display to be impervious to more various uses even under unforgiving conditions is growing, and durability at a higher level than ever before has been required from year to year.

In addition, the liquid crystal display has been increased in size and decreased in thickness mainly in TV applications in recent years, and thus the optical film of a constitutional member is also required to be thinned in accordance therewith. An appropriate hardness and favorable cutting property have been considered to be important for the optical film from the viewpoint of workability as well, and the thinned optical film is further required to be improved in the hardness and cutting property.

In the optical film using a cellulose acylate film, it is known that a specific compound is contained in the film, for further improvement in the performance, or in order to solve various problems in the properties as an optical film or the production thereof.

For example, it is proposed an organic acid compound with pKa of 2 to 7 (see Patent Literature 1), in order to suppress the fluctuation of the retardation of the optical film due to the environmental humidity.

On the other hand, in a silver halide photographic light-sensitive material which is a color negative film rather than the optical film, it is proposed to use a particular hydroxyamine compound, in order to improve storability of the latent image ranging from after photographing to development (for example, see Patent Literature 2). However, a working latent image of the silver halide does not exist in the optical film.

CITATION LIST

Patent Literature

Patent Literature1: JP-A-2011-118135 ("JP-A" means unexamined published Japanese patent application)
Patent Literature2: JP-A-8-62767

Technical Problem

Recently, the liquid crystal display has been used in various environment and it was found that if an optical film with a hard coat layer for a polarizing plate (a protective film for a polarizing plate) is exposed for a long time under light irradiation, such as Xe, peeling occurs between the optical film and the hard coat layer. Thereby it was found that it is necessary to enhance more adhesiveness between the optical film and the hard coat layer, that is to say, to enhance light-resistant adhesiveness. However, although durability of the polarizer was improved by the conventional organic acid compound with pKa of 2 to 7, improvement of such light-resistant adhesiveness was not always enough. In order to exhibit effects over a long period of time under an unforgiving condition, a high stability of the compound itself which improves light-resistant adhesiveness is also needed.

In view of the foregoing, the task of the present invention is to provide an optical film which is excellent in light-resistant adhesiveness over a long period of time, a polarizing plate and a liquid crystal display using the same. Further, the task of the present invention is to provide an optical film whose light-resistant adhesiveness is maintained even over a long period of time by a compound which is excellent in stability, a polarizing plate and a liquid crystal display using the same.

Solution to Problem

The inventors of the present invention have studied on a relationship between light-resistant adhesiveness and a chemical structure by adding various compounds to the optical film. As a result, we found that a hydroxyamine compound is effective for this purpose. Further, we found that stability of the compound itself is improved by a particular electron-attracting substituent in the hydroxylamine skeleton, and thereby the present invention has been completed.

According to the present invention, there is provided the following means:

<1> An optical film, containing a cellulose acylate, and at least one compound represented by any of formulas (I) to (III):

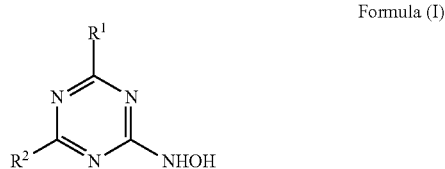

Formula (I)

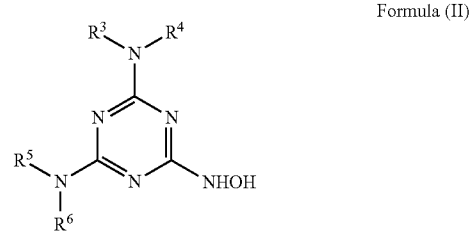

Formula (II)

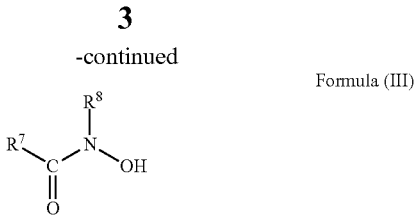

Formula (III)

In the formulas (I) to (III), $R^1$ and $R^2$ each independently represent a halogen atom, an alkyl group, a cycloalkyl group, an alkenyl group, an aryl group, a hydroxy group, a hydroxyamino group, an amino group, an alkylamino group, an arylamino group, an alkoxy group, an aryloxy group, an alkylthio group, or an arylthio group (however, $R^1$ and $R^2$ do not represent an amino group, an alkylamino group, or an arylamino group at the same time); $R^3$ to $R^6$ each independently represent a hydrogen atom, an alkyl group, a cycloalkyl group, an alkenyl group, an aryl group, an acyl group, an alkyl- or aryl-sulfonyl group, an alkyl- or aryl-sulfinyl group, a carbamoyl group, a sulfamoyl group, an alkoxycarbonyl group, or an aryloxycarbonyl group; $R^7$ represents an alkyl group, a cycloalkyl group, an alkenyl group, an aryl group, an alkylamino group, an arylamino group, an alkoxy group, an aryloxy group, or a heterocyclic group; $R^8$ represents an alkyl group, a cycloalkyl group, an alkenyl group, an aryl group, or a heterocyclic group; and each of $R^1$ to $R^8$ may be further substituted with a substituent.

<2> The optical film as described in the item <1>, further containing at least one compound represented by formula (BA):

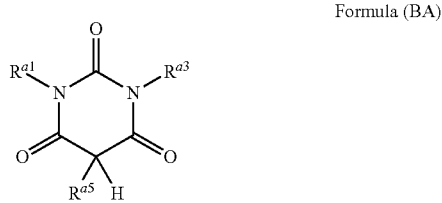

Formula (BA)

In the formula (BA), $R^{a1}$, $R^{a3}$ and $R^{a5}$ each independently represent a hydrogen atom, an alkyl group having 1 to 20 carbon atoms, a cycloalkyl group having 3 to 20 carbon atoms, an alkenyl group having 2 to 20 carbon atoms, or an aryl group having 6 to 20 carbon atoms; herein, the alkyl group, the cycloalkyl group, the alkenyl group, and the aryl group may have a substituent.

<3> The optical film as described in the item <2>, wherein any one of $R^{a1}$, $R^{a3}$ and $R^{a5}$ in the compound represented by formula (BA) is an aralkyl group, or the cycloalkyl group, and the sum of ring structures which exist in $R^{a1}$, $R^{a3}$ and $R^{a5}$ is 3 or more.

<4> The optical film as described in any one of the items <1> to <3>, wherein the total acyl substitution degree (A) of the cellulose acylate satisfies formula:

$1.5 \leq A \leq 3.0$.

<5> The optical film as described in any one of the items <1> to <4>, wherein the acyl group of the cellulose acylate is an acetyl group, and the total acetyl substitution degree (B) of the cellulose acylate satisfies formula:

$2.0 \leq B \leq 3.0$.

<6> The optical film as described in any one of the items <1> to <5>, wherein a thickness of the optical film is from 5 μm to 80 μm.

<7> A polarizing plate containing the optical film as described in any one of the items <1> to <6>.

<8> A liquid crystal display containing the polarizing plate as described in the item <7>.

Note that, in this specification, any numerical expressions in a style of " . . . to . . . " will be used to indicate a range including the lower and upper limits represented by the numerals given before and after "to", respectively.

Herein, in this specification, unless otherwise specified, a group, which is able to have a substituent (for example, a group having an alkyl moiety, an aryl moiety, or a heterocyclic moiety), may have a substituent. For example, the alkyl group is an alkyl group, which may have a substituent, and the aryl group or the aromatic group is an aryl group or an aromatic group, each of which may have a substituent.

In addition, in the case where any atom has at least two substituents and the case where each of the adjacent bonded atoms has a substituent, these substituents may bond to each other to form a ring.

Moreover, in the case where a plurality of groups represented by the same symbol are present and the case where a plurality of groups represented by the same symbol are present as a result of a plurality of repeatings, these may be the same as or different from each other.

When a plurality of substituents, linking groups or the like (hereinafter, referred to as "substituents or the like") are simultaneously or alternatively defined herein, respective substituents or the like may be the same as or different from each other.

Advantageous Effects of Invention

The present invention is able to provide an optical film which is excellent in light-resistant adhesiveness over a long period of time, a polarizing plate and a liquid crystal display using the same. Further, according to the present invention, it has become possible to provide an optical film whose light-resistant adhesiveness is maintained even over a long period of time by a compound which is excellent in stability, a polarizing plate and a liquid crystal display using the same.

Other and further objects, features and advantages of the invention will appear more fully from the following description, appropriately referring to the accompanying drawings.

DETAILED DESCRIPTION OF THE INVENTION

Figure 1:
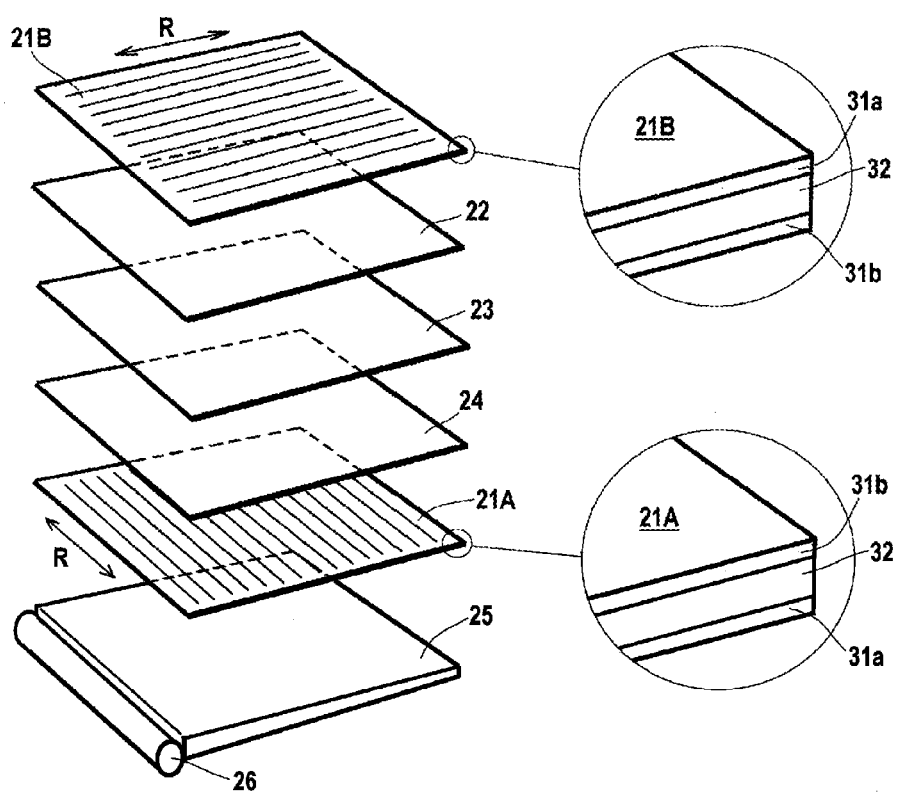
FIG. 1 is an example diagrammatically showing an internal structure of the liquid crystal display of the present invention.

Hereinafter, the present invention is described in detail referring to the embodiments.

<<Optical Film>>

The optical film of the present invention comprised of at least one layer of a cellulose acylate film containing a cellulose acylate and at least one compound represented by any of formulas (I) to (III).

The optical film of the present invention may be a single film of the cellulose acylate film, or alternatively may be a film laminated with a film or a layer composed of a resin component which may be different from the cellulose acylate. In the present invention, an optical film which is laminated with a hard coat layer, so-called an optical film with a hard coat layer, is preferred in particular.

For example, an anti-glare layer, a clear hard coat layer, an antireflective layer, an antistatic layer, and an antifouling layer may be mentioned, in addition to the hard coat layer. It is preferred that any of these layers is/are provided on the hard coat layer. The optical film of the present invention is useful in various applications, such as a polarizing plate protective film, and a surface protective film disposed on an image display surface.

<<Cellulose Acylate Film>>

The cellulose acylate film may be either a single layer or a layered product having at least two layers, as mentioned above. In the case where the cellulose acylate film is the layered product having at least two layers, a double-layered structure or a three-layered structure is preferable, and a three-layered structure is more preferable. In the case of a three-layered structure, it is preferable to have one layer of a core layer (that is, it is the thickest layer, and it is also referred to as the base layer hereinafter), and a skin layer A and a skin layer B, which sandwich the core layer. That is to say, the cellulose acylate film of the present invention preferably has the three-layered structure formed of: skin layer B/core layer/skin layer A. The skin layer A is a layer brought into contact with the metal support, which will be described below, and the skin layer B is a layer at the interface with the air on the side opposite to the metal support, when the cellulose acylate film is produced by the solution film formation. It is noted that, generally, both the skin layer A and the skin layer B are also referred to as a skin layer (or a surface layer).

In the present invention, the cellulose acylate film contains a cellulose acylate, and at least one compound represented by any of formulas (I) to (III).

<Compound Represented by any of Formulas (I) to (III)>

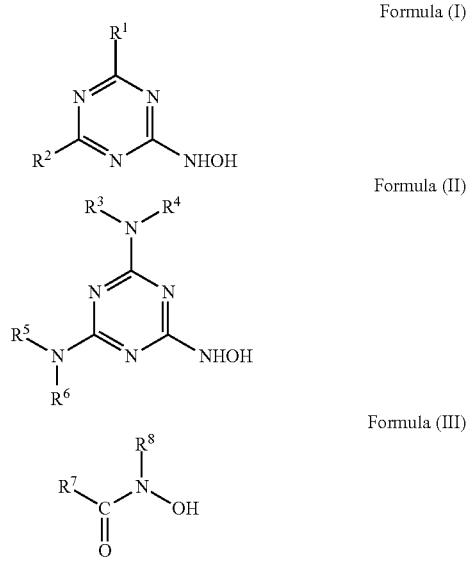

In the formulas (I) to (III), $R^1$ and $R^2$ each independently represent a halogen atom, an alkyl group, a cycloalkyl group, an alkenyl group, an aryl group, a hydroxy group, a hydroxyamino group, an amino group, an alkylamino group, an arylamino group, an alkoxy group, an aryloxy group, an alkylthio group, or an arylthio group. However, $R^1$ and $R^2$ do not represent an amino group, an alkylamino group, or an arylamino group at the same time. $R^3$ to $R^6$ each independently represent a hydrogen atom, an alkyl group, a cycloalkyl group, an alkenyl group, an aryl group, an acyl group, an alkyl- or aryl-sulfonyl group, an alkyl- or aryl-sulfinyl group, a carbamoyl group, a sulfamoyl group, an alkoxycarbonyl group, or an aryloxycarbonyl group. $R^7$ represents an alkyl group, a cycloalkyl group, an alkenyl group, an aryl group, an alkylamino group, an arylamino group, an alkoxy group, an aryloxy group, or a heterocyclic group. $R^8$ represents an alkyl group, a cycloalkyl group, an alkenyl group, an aryl group, or a heterocyclic group. Each of $R^1$ to $R^8$ may be further substituted with a substituent.

Deterioration of the light-resistant adhesiveness is though to be due to deterioration of the cellulose acylate layer that is caused by radical species generated upon light irradiation. The present inventors presume that the compound represented by any of formulas (I) to (III) used in the present invention has a hydroxylamine as a basic skeleton thereof, and the >N—OH moiety scavenges the generated radical species.

On the other hand, it is often the case where the compound having a hydroxylamine as a basic skeleton thereof exhibits low thermal stability in terms of the compound itself. However, the thermal stability is enhanced by substituting a particular electron-withdrawing group for a substituent which binds to a nitrogen atom in the >N—O— structure of the basic skeleton, or a carbon atom adjacent to the foregoing nitrogen atom.

$R^1$ to $R^8$ are preferably a hydrogen atom, or a group having not more than 20 carbon atoms, from the viewpoint of micsibility with the cellulose acylate.

The halogen atom in $R^1$ and $R^2$ includes a fluorine atom, a chlorine atom, a bromine atom, and an iodide atom, and a fluorine atom, a chlorine atom, and a bromine atom are preferred.

The number of carbon atoms of the alkyl group in $R^1$ to $R^8$ is preferably 1 to 20, and more preferably 1 to 14. In $R^7$, the number is more preferred to 4 to 14, while in $R^8$, the number is more preferred to 1 to 6, and 1 or 2 is particularly preferred. Examples of the alkyl group include methyl, ethyl, propyl, isopropyl, n-butyl, isobutyl, t-butyl, n-hexyl, 2-ethylhexyl, n-octyl, decyl, and dodecyl.

The number of carbon atoms of the cycloalkyl group in $R^1$ to $R^8$ is preferably 3 to 20, and more preferably 5 to 12. Examples of the cycloalkyl group include cyclopropyl, cyclopentyl, and cyclohexyl, and cyclopentyl and cyclohexyl are preferred, and cyclohexyl is more preferred.

The number of carbon atoms of the alkenyl group in $R^1$ to $R^8$ is preferably 2 to 20, and more preferably 2 to 12. Examples of the alkenyl group include vinyl, allyl, 2-hexenyl, and oleyl.

The number of carbon atoms of the aryl group in $R^1$ to $R^8$ is preferably 6 to 20, and more preferably 6 to 12. Examples of the aryl group include phenyl, tolyl, and naphthyl, and a phenyl group which may have a substituent is preferred. Examples of the substituent include the substituent S described below.

The number of carbon atoms of the heterocyclic group in $R^7$ to $R^8$ is preferably 0 to 20, more preferably 1 to 12, and still more preferably 2 to 10. As for the hetero ring of the heterocyclic group, the hetero atom which constitutes the hetero ring is preferably a nitrogen atom, or an oxygen atom, and the hetero ring is preferably a 5-membered ring or a 6-membered ring. The hetero ring may be an aromatic ring or a saturated ring. Examples of the hetero ring include a furane ring, a thiophene ring, a pyrrole ring, a pyrazole ring, an oxazole ring, a thiazole, ring, a pyridine ring, a tetrahydrofurane ring, a tetrahydrothiophene ring, a pyrrolidine ring, a piperizine ring, a piperazine ring, a morpholine ring, and a thiomorpholine ring. Any of these hetero rings may be further ring-fused with a benzene ring.

The number of carbon atoms of the alkylamino group in $R^1$, $R^2$ and $R^8$ is preferably 1 to 20, more preferably 1 to 18, and still more preferably 1 to 16. The alkylamino group includes an alkylamino group and a dialkylamino group. Examples thereof include methylamino, ethylamino, hexylamino, octylamino, decylamino, dodecylamino, 3-ethoxypropyl, dimethylamino, diethylamino, N,N-bis(3-ethoxypropyl)amino, N,N-bis(2-ethylhexyl)amino, dioctylamino, and didecylamino.

The number of carbon atoms of the arylamino group in $R^1$, $R^2$ and $R^8$ is preferably 6 to 20, more preferably 6 to 18, and still more preferably 6 to 16. The arylamino group includes an N-alkyl-N-arylamino group and a diarylamino group. Examples thereof include phenylamino, diphenylamino, and N-methyl-N-phenylamino The number of carbon atoms of the alkoxy group in $R^1$, $R^2$ and $R^7$ is preferably 1 to 20, more preferably 1 to 12, and still more preferably 1 to 8. Examples of the alkoxy group include methoxy, ethoxy, isopropoxy, n-propyloxy, n-hexyloxy, 2-ethylhexyloxy, and dodecyloxy.

The number of carbon atoms of the aryloxy group in $R^1$, $R^2$ and $R^7$ is preferably 6 to 20, and more preferably 6 to 12. Examples of the aryloxy group include phenoxy and naphthoxy, and a phenoxy group which may have a substituent is preferred. Examples of the substituent include the substituent S described below.

The number of carbon atoms of the alkylthio group in $R^1$, $R^2$ and $R^7$ is preferably 1 to 20, more preferably 1 to 12, and still more preferably 1 to 8. Examples of the alkylthio group include methylthio, ethylthio, isopropylthio, n-propylthio, n-hexylthio, 2-ethylhexylthio, and dodecylthio.

The number of carbon atoms of the arylthio group in $R^1$, $R^2$ and $R^7$ is preferably 6 to 20, and more preferably 6 to 12. Examples of the arylthio group include phenylthio and naphthylthio, and a phenylthio group which may have a substituent is preferred. Examples of the substituent include the substituent S described below.

The number of carbon atoms of the acyl group in $R^3$ to $R^6$ is preferably 1 to 20, and more preferably 2 to 12. The acyl group includes a formyl group, an alkylcarbonyl group, a cycloalkylcarbonyl group, an alkenylcarbonyl group, an arylcarbonyl group, and a heterocyclic carbonyl group. Examples thereof include formyl, acetyl, propionyl, butyryl, isobutyryl, pivaloyl, lauroyl, myristoyl, acryloyl, methacryloyl, cyclopropylcarbonyl, benzoyl, naphthoyl, nicotinoyl, and isonicotinoyl.

The number of carbon atoms of the alkyl- or aryl-sulfonyl group in $R^3$ to $R^6$ is preferably 1 to 20, and more preferably 1 to 12. Note that the lower limit of the number of carbon atoms of the aryl-sulfonyl group is 6. Examples of the alkyl- or aryl-sulfonyl group include methylsulfonyl, 2-ethylhexylsulfonyl, benzenesulfonyl, toluenesulfonyl, and naphthalenesulfonyl.

The number of carbon atoms of the alkyl- or aryl-sulfinyl group in $R^3$ to $R^6$ is preferably 1 to 20, and more preferably 1 to 12. Note that the lower limit of the number of carbon atoms of the aryl-sulfinyl group is 6. Examples of the alkyl- or aryl-sulfinyl group include methylsulfinyl, 2-ethylhexylsulfinyl, benzenesulfinyl, toluenesulfinyl, and naphthalenesulfinyl.

The number of carbon atoms of the carbamoyl group in $R^3$ to $R^6$ is preferably 1 to 20, and more preferably 2 to 12. The carbamoyl group includes a —C(=O)NH$_2$ group, and an alkyl- or aryl-carbamoyl group, and the lower limit of the number of carbon atoms of the aryl-carbamoyl group is 6. Examples of the carbamoyl group include carbamoyl, N-methylcarbamoyl, N,N-diethylcarbamoyl, N-(2-ethylhexyl)carbamoyl, phenylcarbamoyl, N-methyl-N-phenylcarbamoyl, and N,N-diphenylcarbamoyl.

The number of carbon atoms of the sulfamoyl group in $R^3$ to $R^6$ is preferably 0 to 20, and more preferably 1 to 12. The sulfamoyl group includes a —SO$_2$NH$_2$ group, and an alkyl- or aryl-sulfamoyl group, and the lower limit of the number of carbon atoms of the aryl-sulfamoyl group is 6. Examples of the sulfamoyl group include sulfamoyl, N-methylsulfamoyl, N,N-diethylsulfamoyl, N-(2-ethylhexyl)sulfamoyl, phenylsulfamoyl, N-methyl-N-phenylsulfamoyl, and N,N-diphenylsulfamoyl.

The number of carbon atoms of the alkoxycarbonyl group in $R^3$ to $R^6$ is preferably 2 to 20, and more preferably 2 to 12. Examples of the alkoxycarbonyl group include methoxycarbonyl, ethoxycarbonyl, and 2-ethylhexyloxycarbonyl.

The number of carbon atoms of the aryloxycarbonyl group in $R^3$ to $R^6$ is preferably 7 to 20, and more preferably 7 to 12. Examples of the aryloxycarbonyl group include phenoxycarbonyl, and naphthoxycarbonyl.

As for $R^1$ and $R^2$, an alkyl group, a cycloalkyl group, an alkenyl group, an aryl group, a hydroxyamino group, an alkylamino group, an arylamino group, an alkoxy group, and an aryloxy group are preferred. An alkyl group, a cycloalkyl group, an alkenyl group, an aryl group, a hydroxyamino group, an alkylamino group, and an alkoxy group are more preferred. An alkyl group, a cycloalkyl group, an alkylamino group, and an alkoxy group are still more preferred.

Note that when $R^1$ is a hydroxyamino group, it is preferred in terms of good miscibility with a cellulose acylate that $R^2$ is a halogen atom, an alkyl group, a cycloalkyl group, an alkenyl group, an aryl group, a hydroxy group, an amino group, an alkylamino group, an arylamino group, an alkoxy group, an aryloxy group, an alkylthio group, or an arylthio group.

As for $R^3$ to $R^6$, a hydrogen atom, an alkyl group, a cycloalkyl group, an alkenyl group, an aryl group, and an acyl group are preferred. A hydrogen atom, an alkyl group, a cycloalkyl group, and an alkenyl group are more preferred. A hydrogen atom, an alkyl group, and a cycloalkyl group are still more preferred. A hydrogen atom, an alkyl group having 4 to 14 carbon atoms, and a cycloalkyl group having 5 to 14 carbon atoms are still more preferred.

The case where any one of $R^3$ to $R^6$ is an alkyl group, a cycloalkyl group, an alkenyl group, an aryl group, an acyl group, an alkyl- or aryl-sulfonyl group, an alkyl- or aryl-sulfinyl group, a carbamoyl group, a sulfamoyl group, an alkoxycarbonyl group, or an aryloxycarbonyl group is preferred from the viewpoint of miscibility with a cellulose acylate.

Among $R^3$ to $R^6$, the number of groups which represent a hydrogen atom is preferably 0 to 3, more preferably 0 to 2, and still more preferably 2.

As for $R^7$, an alkyl group, a cycloalkyl group, an alkenyl group, and an aryl group are preferred. An alkyl group, a cycloalkyl group, and an alkenyl group are more preferred. An alkyl group is still more preferred.

As for $R^8$, an alkyl group, a cycloalkyl group, and an alkenyl group are preferred. An alkyl group and a cycloalkyl group are more preferred. An alkyl group having 1 to 6 carbon atoms and a cycloalkyl group having 5 to 12 carbon atoms are still more preferred. An alkyl group having 1 to 2 carbon atoms is most preferred.

Optionally, each group of $R^1$ to $R^8$ may have a substituent. Examples of the substituent include the substituent S described below. Preferable examples thereof include an aralkyl group which is an alkyl group substituted with an aryl group, for example, benzyl, phenethyl, and 3-phenylpropyl are preferred.

The molecular weight of the compound represented by any of formulas (I) to (III) is preferably 200 to 3,000, more preferably 200 to 2,000, and still more preferably 250 to 1,000.

Hereinafter, specific examples of the compound represented by any of formulas (I) to (III) to be used in the present invention are shown. However, the present invention is not limited by these exemplified examples.

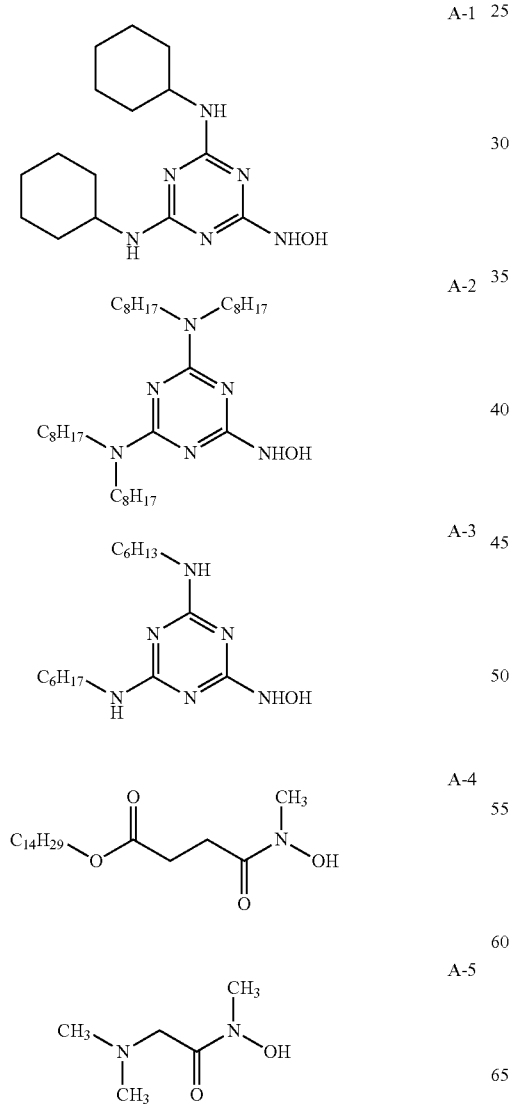

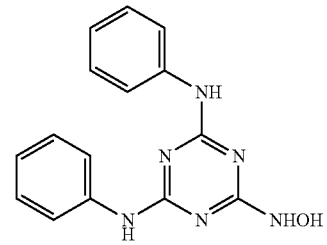

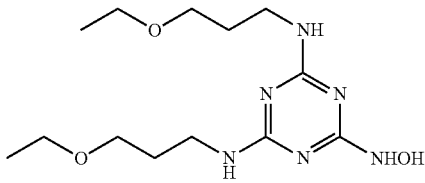

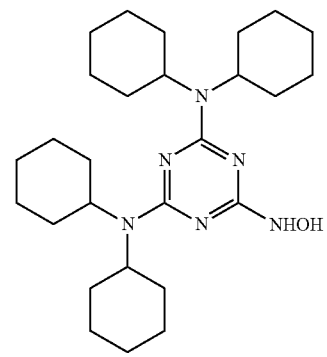

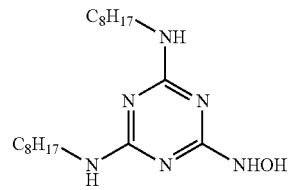

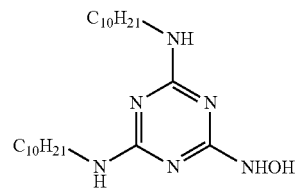

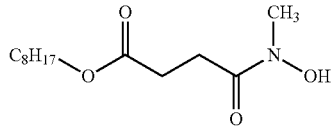

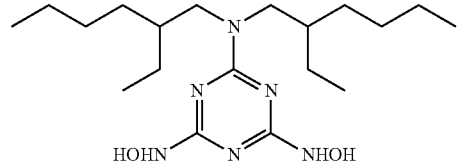

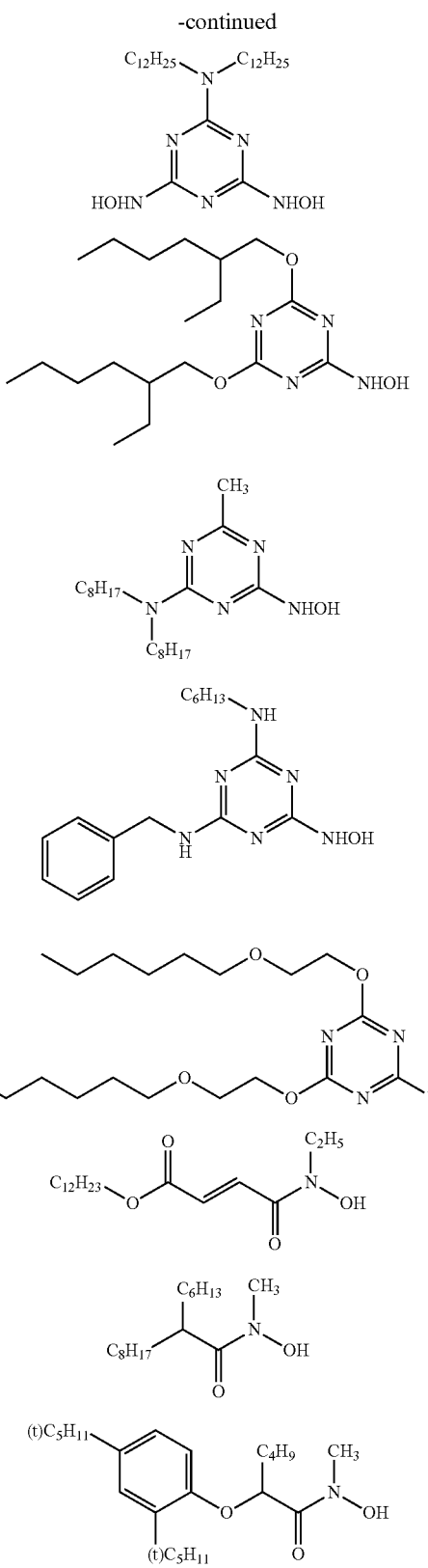

Further, compounds described in JP-A-8-62767, JP-A-8-194277 and JP-A-8-114884 may also be preferably used.

The compound represented by any of formulas (I) to (III) to be used in the present invention may be easily synthesized by the methods described in J. Org. Chem., 27, 4054 (1962), J. Amer. Chem. Soc., 73, 2981 (1951), JP-B-49-10692 ("JP-B" means examined published Japanese patent application), and the like, or methods based on these methods.

The compound represented by any of formulas (I) to (III) may be used singly, or in combination of two or more selected from these compounds.

The content of the compound represented by any of formulas (I) to (III) is preferably from 0.01 to 4 parts by mass, more preferably from 0.01 to 3 parts by mass, and still more preferably from 0.02 to 2 parts by mass, with respect to 100 parts by mass of the cellulose acylate.

<Barbituric Acid Compound>

In the present invention, the compound represented by any of formulas (I) to (III) may be used together with other compounds in combination. As for the compound to be used in combination, a barbituric acid compound is preferred.

By using in combination with the barbituric acid compound, durability of the polarizing plate is improved, and in addition, coloration of the film due to light is suppressed, and light-resistant adhesiveness is also improved.

The content of the barbituric acid compound is preferably 0.1 to 20 parts by mass, more preferably 0.2 to 15 mass parts, and still more preferably 0.3 to 10 parts by mass, to 100 parts by mass of the cellulose acylate.

Further, the content of the barbituric acid compound is preferably 1 to 100,000 parts by mass, more preferably 10 to 10,000 mass parts, and still more preferably 100 to 10,000 parts by mass, to 100 parts by mass of the compound of any of formula (I) to (III).

The barbituric acid compound is preferably a compound represented by formula (BA).

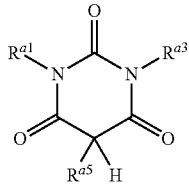

Formula (BA)

In formula (BA), $R^{a1}$, $R^{a3}$, and $R^{a5}$ each independently represent a hydrogen atom, an alkyl group with 1 to 20 carbon atoms, a cycloalkyl group with 3 to 20 carbon atoms, an alkenyl group with 2 to 20 carbon atoms, or an aryl group with 6 to 20 carbon atoms. Each group of the alkyl group, the cycloalkyl group, the alkenyl group, or the aryl group, by $R^{1a}$, $R^{3a}$ and $R^{5b}$, may be substituted with a substituent.

As for the alkyl group, the cycloalkyl group, the alkenyl group, and the aryl group in $R^{a1}$, $R^{a3}$ and $R^{a5}$, the number of carbon atoms thereof is preferably the same as the alkyl group, the cycloalkyl group, the alkenyl group, and the aryl group in the above-described $R^1$ and $R^2$ in formulas (I) to (III), and the same specific groups may be exemplified.

Any one of $R^{a1}$, $R^{a3}$ and $R^{a5}$ is preferably an aralkyl group or a cycloalkyl group. As for the aralkyl group, a benzyl group is preferable. As for the cycloalkyl group, a cyclopentyl group and cyclohexyl group are preferable, and a cyclohexyl group is more preferable.

The total number of ring structures existing in $R^{a1}$, $R^{a3}$ and $R^{a5}$ is preferably 3 or more. The ring of the ring structure includes an aromatic ring and an aliphatic ring. The carbon atom of these rings may be substituted with a hetero atom. As for the ring structure, a benzene ring, a naphthalene ring, a cyclopentane ring, and a cyclohexane ring are preferable, and a benzene ring and a cyclohexane ring are more preferable.

It is more preferable for each of $R^{a1}$, $R^{a3}$ and $R^{a5}$ to have one or more ring structures, and it is still more preferable for each of $R^{a1}$, $R^{a3}$ and $R^{a5}$ to have one ring structure.

The total number of ring structures is preferably 3 to 6, more preferably 3 or 4.

The molecular weight of the compound represented by formula (BA) is preferably 250 to 1,200, more preferably 300 to 800, and particularly preferably 350 to 600.

By setting the molecular weight to such a preferable range, a high-transparent film which is excellent in inhibiting volatilization of the compound to be used in the present invention from the film, can be obtained.

Hereinafter, specific examples of the barbituric acid compound are shown, but the present invention is not limited thereto.

Herein, "Ph" represents a phenyl group, "cHex" represents a cyclohexyl group, and "$C_6H_4$" represents a phenylene group. A group of ( ), such as $C_6H_4$(p-$CH_3$), represents a substituent to the phenyl group, and "p-" indicates that the group is at the p-position.

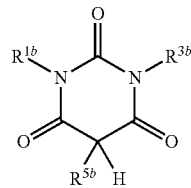

| Compound No. | $R^{1b}$ | $R^{3b}$ | $R^{5b}$ |
|---|---|---|---|
| BA-1 | Ph | $CH_2Ph$ | $CH_2Ph$ |
| BA-2 | H | $CH_2Ph$ | Ph |
| BA-3 | H | H | Ph |
| BA-4 | H | H | $CH_2Ph$ |
| BA-5 | H | H | $CHPh_2$ |
| BA-6 | H | H | $CH_2C_6H_4$(p-$CH_3$) |
| BA-7 | H | H | $CH_2C_6H_4$(p-$OCH_3$) |
| BA-8 | H | H | $CH_2C_6H_4$(p-Cl) |
| BA-9 | $CH_3$ | $CH_3$ | Ph |
| BA-10 | $CH_3$ | $CH_3$ | $CH_2Ph$ |
| BA-11 | H | Ph | Ph |
| BA-12 | H | Ph | $CH_2Ph$ |
| BA-13 | H | $CH_2Ph$ | $CH_2Ph$ |
| BA-14 | H | $CHPh_2$ | Ph |
| BA-15 | H | cHex | cHex |
| BA-16 | Ph | Ph | Ph |
| BA-17 | Ph | Ph | $CH_2Ph$ |
| BA-18 | Ph | Ph | n-$C_4H_9$ |
| BA-19 | Ph | Ph | $CH(CH_3)Ph$ |
| BA-20 | Ph | $C_6H_4$(p-$CH_3$) | Ph |
| BA-21 | Ph | $C_6H_4$(p-$OCH_3$) | $CH_2Ph$ |
| BA-22 | Ph | $CH_2Ph$ | $CH_2CH_2Ph$ |
| BA-23 | Ph | $CH_2Ph$ | $CH_2Ph$ |
| BA-24 | cHex | cHex | Ph |
| BA-25 | cHex | cHex | $CH_2Ph$ |
| BA-26 | cHex | cHex | cHex |
| BA-27 | $CH_2Ph$ | $CH_2Ph$ | Ph |
| BA-28 | $CH_2Ph$ | $CH_2Ph$ | $CH_2Ph$ |
| BA-29 | $CH_2Ph$ | $CH_2Ph$ | n-$C_4H_9$ |
| BA-30 | Ph | Ph | $CH_2CH_2CN$ |
| BA-31 | Ph | Ph | $CH_2CH_2COOC_2H_5$ |
| BA-32 | Ph | $CH_2CH_2OCH_3$ | Ph |
| BA-33 | Ph | $CH_2CH_2COOC_2H_5$ | $CH_2Ph$ |
| BA-34 | Ph | $CH_2CH_2OH$ | $CH_2Ph$ |
| BA-35 | $CH_3$ | $CH_3$ | n-$C_4H_9$ |

The compound represented by formula (BA) is known to be able to synthesize by a method of synthesizing barbituric acid, based on condensation of a urea derivative with a malonic acid derivative. The barbituric acid having two substituents on the N atoms may be obtained, by heating a N,N'-disubstituted urea with malonyl chloride, or by heating with a combination of malonic acid and an activator, such as acetic anhydride. For example, methods described in: Journal of the American Chemical Society, vol. 61, p. 1015 (1939), Journal of Medicinal Chemistry, vol. 54, p. 2409 (2011), Tetrahedron Letters, vol. 40, p. 8029 (1999), and WO2007/150011, are preferably used.

Further, both unsubstituted and substituted malonic acids are acceptable for use in the condensation. By subjecting the barbituric acid unsubstituted at the 5-position, which is obtainable by condensing unsubstituted malonic acid with an urea derivative, various barbituric acid compounds are obtained, by modifying the thus-obtained compound.

Herein, a description of the substituent S is given.

In the present specification, the term "substituent" is referred to the substituent S, unless otherwise specified. Unless otherwise specified, each of the groups defined in the formulas (I) to (III), formula (BA) and the like may have a substituent, and as for the substituent, the substituent S is referenced.

[Substituent S]

The substituent S include: alkyl groups (preferably those having from 1 to 20 carbon atoms, for example, methyl, ethyl, isopropyl, t-butyl, pentyl, heptyl, 1-ethylpentyl, 2-ethylhexyl, benzyl, 2-ethoxyethyl, 1-carboxymethyl); alkenyl groups (preferably those having from 2 to 20 carbon atoms, for example, vinyl, allyl, oleyl); alkynyl groups (preferably those having from 2 to 20 carbon atoms, for example, ethynyl, 2-propinyl, 2-butynyl, phenylethynyl); cycloalkyl groups (preferably those having from 3 to 20 carbon atoms, for example, cyclopropyl, cyclopentyl, cyclohexyl, 4-methylcyclohexyl); aryl groups (preferably those having from 6 to 20 carbon atoms, for example, phenyl, 1-naphtyl, 4-methoxyphenyl, 2-chlorophenyl, 3-methylphenyl); heterocyclic groups (preferably those having from 0 to 20 carbon atoms and preferably those having a ring-constituting heteroatom selected from an oxygen atom, a nitrogen atom, or a sulfur atom, and preferably those having a 5- or 6-membered ring which may be condensed with a benzene ring or a hetero ring, and the ring may be a saturated ring, an unsaturated ring, or an aromatic ring, for example, 2-pyridyl, 4-pyridyl, 2-imidazolyl, 2-benzoimidazolyl, 2-thiazolyl, 2-oxazolyl); alkoxy groups (preferably those having from 1 to 20 carbon atoms, for example, methoxy, ethoxy, isopropyloxy, benzyloxy); aryloxy groups (preferably those having from 6 to 20 carbon atoms, for example, phenoxy, 1-naphthyloxy, 3-methylphenoxy, 4-methoxyphenoxy); alkylthio groups (preferably those having from 1 to 20 carbon atoms, for example, methylthio, ethylthio, isopropylthio, benzylthio); arylthio groups (preferably those having from 6 to 20 carbon atoms, for example, phenylthio, 1-naphtylthio, 3-methylphenylthio, 4-methoxyphenylthio); acyl groups (those including an alkylcarbonyl group, an alkenylcarbonyl group, an arylcarbonyl group, and a heterocyclic carbonyl group, and preferably having 20 or less carbon atoms, for example, acetyl, pivaloyl, acryloyl, methacryloyl, benzoyl, nicotinoyl); alkoxycarbonyl groups (preferably those having from 2 to 20 carbon atoms, for example, ethoxycarbonyl, 2-ethylhexyloxycarbonyl); aryloxycarbonyl groups (preferably those having from 7 to 20 carbon atoms, for example, phenyloxycarbonyl, naphthyloxycarbonyl); amino groups (those including an amino group, an alkylamino group, an arylamino group, and a heterocyclic amino group, and preferably having from 0 to 20 carbon atoms, for example, amino, N,N-dimethylamino, N,N-diethylamino, N-ethylamino, anilino, 1-pyrrolidinyl, piperidino, morpholinyl); alkyl- or aryl-sulfonamido groups (preferably those having from 0 to 20 carbon atoms, for example, N,N-dimethylsulfonamido, N-phenylsulfonamido); unsubstituted-, alkyl- or aryl-sulfamoyl groups (preferably those having from 0 to 20 carbon atoms, for example, N,N-dimethylsulfamoyl, N-phenylsulfamoyl); acyloxy groups (preferably those having from 1 to 20 carbon atoms, for example, acetyloxy, benzoyloxy); unsubstituted-, alkyl- or aryl-carbamoyl groups (preferably those having from 1 to 20 carbon atoms, for example, N,N-dimethylcarbamoyl, N-phenylcarbamoyl); acylamino groups (preferably those having from 1 to 20 carbon atoms, for example, acetylamino, acryloylamino, benzoylamino, nicotineamido); a cyano group; a hydroxy group; a mercapto group; and a halogen atom (for example, fluorine atom, chlorine atom, bromine atom, iodine atom).

Any of these substituents may be further substituted with a substituent. Examples of such a substituent include those exemplified as the substituent S.

Examples thereof include an aralkyl group in which an alkyl group is substituted with an aryl group, and a group in which an alkyl group is substituted with an alkoxycarbonyl group or a cyano group.

<Cellulose Acylate>

In the present invention, cellulose acylate is used as a main component of the cellulose acylate film. One cellulose acylate may be used, or alternatively two or more thereof may be used in combination. The cellulose acylate may be a cellulose acylate having, for example, only an acetyl group as the acyl substituent thereof. Alternatively, a cellulose acylate having a plurality of different acyl substituents as the acyl substituent thereof may be used. The cellulose acylate may be a mixture of cellulose acylates that are different from one another. Note that the expression "main component" means that the cellulose acylate is contained at a ratio of 50% by mass or more in a resin component which composes a film or a layer, and the content of the cellulose acylate in the resin component is preferably 60% by mass or more, and more preferably 80% by mass or more.

The cellulose material for cellulose acylate which is used in the present invention includes cotton liter and wood pulp (hardwood pulp, softwood pulp), and cellulose acylate obtained from any of such a cellulose material are usable herein. Those cellulose materials may be mixed for use herein. The cellulose materials are described, for example, in Marusawa & Uda's "Plastic Material Lecture (17), Cellulose Resin" by Nikkan Kogyo Shinbun (1970) and Hatsumei Kyokai's Disclosure Bulletin 2001-1745 (pp. 7-8), and those celluloses described therein may be usable herein.

In the present invention, the acyl group of the cellulose acylate may be one acyl group, or two or more acyl groups. It is preferable that the cellulose acylate to be used in the present invention has an acyl group having 2 or greater carbon atoms as a substituent. The acyl group having 2 or greater carbon atoms is not particularly limited, such that it may be an aliphatic acyl group or an aromatic acyl group. Examples thereof include cellulosic alkylcarbonyl ester groups, alkenylcarbonyl ester groups, aromatic carbonyl ester groups, and aromatic alkylcarbonyl ester groups, each of which may have a substituted group. Preferable examples thereof include acetyl, propionyl, butanoyl, heptanoyl, hexanoyl, octanoyl, decanoyl, dodecanoyl, tridecanoyl, tetradecanoyl, hexadecanoyl, octadecanoyl, isobutanoyl, tert-butanoyl, cyclohexane carbonyl, oleoyl, benzoyl, naphthylcarbonyl, and cinnamoyl. Among these, more preferred are acetyl, propionyl, butanoyl, decanoyl, octadecanoyl, tert-butanoyl, oleoyl, benzoyl, naphthylcarbonyl, cinnamoyl, and the like. Further preferred are acetyl, propionyl, and butanoyl.

It is preferable that the cellulose acylate to be used in the present invention has an acyl group having 2 to 4 carbon atoms as a substituent. When two or more acyl groups are used, it is preferable that one kind of the acyl groups is an acetyl group and another kind of the acyl group having 2 to 4 carbon atoms is preferably a propionyl group or a butyryl group. By use of these cellulose acylates, a solution with a good solubility can be prepared. Especially in a non-chlorine organic solvent, preparation of a good solution becomes possible with those cellulose acylates. Further, preparation of a solution having a low viscosity and a good filterability becomes possible.

In the present invention, it is especially preferable that the cellulose acylate has an acetyl group only as an acyl group, from the viewpoint of effectively improving the hardness owing to the compound represented by any of formulas (I) to (III).

Hereinafter, cellulose acylate to be preferably used in the present invention is described in detail.

The glucose unit having β-1,4 bonds which constitutes cellulose has free hydroxy groups at the 2-, 3-, and 6-positions thereof. The cellulose acylate is a polymeric substance (polymer) in which a part of or all of these hydroxy groups is or are acylated with an acyl group(s).

The acyl substitution degree indicates a degree of acylation of the hydroxy groups located at the 2-, 3-, and 6-positions of cellulose. When each of the hydroxy groups at the 2-, 3-, and 6-positions of all of the glucose units is acylated, the total acyl substitution degree is 3. For example, when each of the hydroxy groups only at the 6-position of all of the glucose units is acylated, the total acyl substitution degree is 1. In the same manner, even if each of the hydroxy groups at either the 6- position or the 2-position of the entire glucose unit is acylated, the total acyl substitution degree is 1.

That is to say, the acyl substitution degree indicates a degree of acylation, provided that when all of the hydroxy groups of the glucose molecule are entirely acylated, the acyl substitution degree is 3.

The details of the method of measuring the acyl substitution degree are described in Tezuka et al. (Carbohydrate, Res., 273 (1995) p. 83 to 91). The acyl substitution degree can be determined according to the method defined in ASTM-D817-96.

When the total acyl substitution degree of the cellulose acylate to be used in the present invention is A, A is preferably from 1.5 to 3.0 (1.5≤A≤3.0), more preferably from 2.00 to 2.97, still further preferably from 2.50 to less than 2.97, and particularly preferably from 2.70 to 2.95.

When the acyl group of the cellulose acylate is only an acetyl group, if we take the total acetyl substitution degree is B, B is preferably from 2.0 to 3.0 (2.0≤B≤3.0), more preferably from 2.0 to 2.97, still more preferably from 2.5 to less than 2.97, especially preferably from 2.55 to less than 2.97, more specially preferably from 2.60 to 2.96, and particularly preferably from 2.70 to 2.95.

In the present specification, the effects of the compound represented by any of formulas (I) to (III) are exerted particularly, with respect to the cellulose acylate in which A that is the total degree of acyl substitution is more than 2.00.

In the case where the cellulose acylate film of the optical film of the present invention is a laminate (multilayer configuration), the degree of acyl group substitution of the cellulose acylate in each layer may be uniform or a plurality of cellulose acrylates which have different degrees of acyl group substitution or different acyl groups may be present in one layer in a mixed manner in the cellulose acylate film.

In the case where an acid anhydride or an acid chloride is used as an acylating agent in acylation of the cellulose, methylene chloride or an organic acid, for example, acetic acid, is used as an organic solvent which acts as a reaction solvent.

As for the catalyst, when the acylating agent is an acid anhydride, a protic catalyst, such as sulfuric acid, is preferably used. While, when the acylating agent is an acid chloride (for example, $CH_3CH_2COCl$), a basic compound is used as the catalyst.

A most common industrial method for the synthesis of a mixed fatty acid ester of cellulose is a method of acylating cellulose with a mixed organic acid component that includes fatty acids corresponding to an acetyl group and to any other acyl group (e.g. acetic acid, propionic acid, valeric acid) or their acid anhydrides.

The cellulose acylate may be produced, for example, according to the method described in JP-A-10-45804.

The film of the present invention contains the cellulose acylate, especially the cellulose acylate film to be used in the present invention in the proportion of preferably from 5 to 99% by mass, more preferably from 20 to 99% by mass, and particularly preferably from 50 to 95% by mass, with respect to the total solid content of the film, from the viewpoint of water-vapor transmission ratio.

<Other Additives>

To the optical film of the present invention, particularly to the cellulose acylate film, a retardation-controlling agent (i.e. a retardation-developing agent and a retardation-reducing agent), and as a plasticizer, a polycondensation ester compound (polymer), and a polyvalent ester of polyvalent alcohol, for example, a phthalic acid ester, a phosphoric acid ester, and the like, and further additives, such as a ultraviolet absorber, an antioxidant, and a matting agent may be added.

In the present specification, when compounds are described, they may be described incorporating therein the expression"-based", for example, like a phosphoric acid ester-based compound. However, in this case, this means the same as the phosphoric acid ester compound.

(Retardation-Reducing Agent)

In the present invention, as a retardation-reducing agent, any compound known as an additive for the cellulose acylate film may be generally utilized.

The polymer retardation-reducing agent is selected from a phosphoric acid ester-based polymer, a styrene-based polymer, an acrylic-based polymer and their copolymers. Of these, an acrylic-based polymer and a styrene-based polymer are preferred. Further, at least one polymer having a negative intrinsic birefringence, such as a styrene-based polymer and an acrylic-based polymer, is preferred.

It is more preferable from the viewpoint of realizing an Nz factor that the above-described retardation-reducing agent is an Rth reducing agent. Of the retardation-reducing agents, examples of the Rth reducing agent include an acrylic-based polymer and a styrene-based polymer, and also a low molecular compound represented by any one of formulae (3) to (7) described in JP-A-2007-272177. Among them, an acrylic-based polymer and a styrene-based polymer are preferred, and an acrylic-based polymer is more preferred.

The content of the retardation-reducing agent is preferably set to the proportion of from 0.01 to 30% by mass, more preferably from 0.1 to 20% by mass, and particularly preferably from 0.1 to 10% by mass, with respect to the cellulosic resin. When the content is set to 30% by mass or less, miscibility with the cellulosic-based resin can be improved, whereby a film excellent in transparency can be produced. When two or more retardation-reducing agents are used, it is preferable that the total content thereof is within the above-described range.

(Retardation-Developing Agent)

The optical film of the present invention may contain at least one retardation-developing agent, in order to develop a value of retardation.

The retardation-developing agent is not particularly limited, and examples thereof include a material including a stick-shaped or disc-shaped compound, and a compound that shows retardation-developing property of the above-described non-phosphoric acid ester-based compounds. As for the stick-shaped or disc-shaped compound, a compound having at least two aromatic rings can be preferably used as the retardation-developing agent.

The content of the retardation-developing agent composed of a stick-shaped compound is preferably from 0.1 to 30 parts by mass, and more preferably from 0.5 to 20 parts by mass, with respect to 100 parts by mass of the polymer component including cellulose acylate.

The disc-shaped compound, when compared to the stick-shaped compound, is excellent in Rth retardation-developing property, and therefore preferably used in the case where particularly large Rth retardation is required. Two or more retardation-developing agents may be used in combination.

The retardation-developing agent preferably has a maximum absorption in the wavelength region of from 250 to 400 nm, and preferably it has substantially no absorption in the visible region.

The details of the retardation-developing agent are described on page 49 of Journal of Technical Disclosure 2001-1745.

The retardation-developing agent composed of a disk-shaped compound is contained in an amount of preferably 0.1 to 30 parts by mass, more preferably 0.5 to 20 parts by mass, to 100 parts by mass of the polymer component including the cellulose acylate.

The disc-shaped compound contained in the retardation-developing agent is preferably less than 3 parts by mass, more preferably less than 2 parts by mass, and particularly preferably less than 1 part by mass, with respect to 100 parts by mass of the cellulose acylate.

[Plasticizer (Hydrophobizing Agent)]

In the optical film, particularly the cellulose acylate film, by containing a plasticizer in a cellulose acylate, the moisture content or degree of moisture permeability (water-vapor transmission ratio) of the cellulose acylate film is lowered, so that hydrolysis reaction of the cellulose acylate due to the moisture in the cellulose acylate film is suppressed. Further, the plasticizer is able to suppress diffusion of the additives from the cellulose acylate film to a polarizer layer under high temperature and high humidity, whereby deterioration of polarizer performance can be improved.

The compound represented by any of formulas (I) to (III) to be used in the present invention can be also used as a plasticizer, by containing it in an optical film, particularly a cellulose acylate film. That is to say, effects of improvement in durability, including control of glass transition temperature and lowering in the moisture content or degree of moisture permeability as described above are obtained, and in addition, hardness of the cellulose acylate film can be also enhanced at the same time. Further, the compound represented by any of formulas (I) to (III) to be used in the present invention is able to produce a hardness-improving effect even if used together with other general-purpose plasticizers, so that a plurality of plasticizers may be used in combination to contain them in the optical film or the cellulose acylate film.

In the present invention, among plasticizers to be used in combination, a polyvalent ester-based plasticizer in which ester groups are packed positionally at close hand in the molecule is preferred. Specifically, the polyvalent ester-based plasticizer includes a polycondensation ester compound (hereinafter, referred to as the polycondensation ester-based plasticizer), a polyvalent ester compound of a polyvalent alcohol (hereinafter, referred to as the polyvalent alcohol ester-based plasticizer), and a carbohydrate compound (hereinafter, referred to as the carbohydrate derivative-based plasticizer). In the present invention, these compounds are excellent in development of the plasticizer effect as described above.

Hereinafter, plasticizers that can be used in the present invention are described in detail.
(Polycondensation Ester-based Plasticizer)

The cellulose acylate film of the present invention preferably contains a polycondensation ester-based plasticizer. By incorporating therein the polycondensation ester-based plasticizer, it is possible to achieve a cellulose acylate film excellent in humidity stability and polarizing plate durability.

The polycondensation ester-based plasticizer is obtained by bringing a divalent carboxylic acid compound and a diol compound into polycondensation.

The polycondensation ester-based plasticizer is preferably obtained, by bringing at least one dicarboxylic acid represented by formula (a) and at least one diol represented by formula (b) into polycondensation.

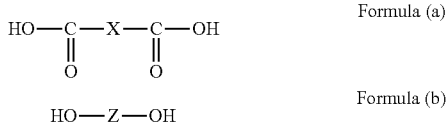

In formulas (a) and (b), X represents a divalent aliphatic group having 2 to 18 carbon atoms, a divalent aromatic group having 6 to 18 carbon atoms, or a divalent hetero ring having 2 to 18 carbon atoms; and Z represents a divalent aliphatic group having 2 to 8 carbon atoms.

The divalent carboxylic acid compound represented by formula (a) includes an aliphatic carboxylic acid and an aromatic or heterocyclic carboxylic acid as described above, and an aliphatic carboxylic acid and an aromatic carboxylic acid are preferred.

On the other hand, the diol compound includes an aromatic or heterocyclic compound, in addition to the aliphatic compound represented by the above-described formula (b).

The polycondensation ester-based plasticizer is preferably obtained from at least one dicarboxylic acid having an aromatic ring (also be called an aromatic dicarboxylic acid) and at least one aliphatic diol having an average number of carbon atoms from 2.5 to 8.0. Further, it is also preferably that the polycondensation ester be obtained from, as a dicarboxylic acid, a mixture of the aromatic dicarboxylic acid and at least one aliphatic dicarboxylic acid, and, as a diol, at least one aliphatic diol having an average number of carbon atoms from 2.5 to 8.0.

The number-average molecular weight of the polycondensation ester-based plasticizer is preferably from 500 to 2,000, more preferably from 600 to 1,500, and still more preferably from 700 to 1,200. When the number-average molecular weight of the polycondensation ester is 600 or greater, volatility becomes lower so that a film failure and a process contamination can be suppressed which is excellent, due to vaporization under the high temperature condition in stretching the cellulose acylate film.

Further, when the number-average molecular weight of the polycondensation ester is 2,000 or less, miscibility with a cellulose acylate becomes higher so that the bleeding can be suppressed which is excellent, in film production and heat-stretching.

In the case where a mixture of an aromatic dicarboxylic acid and an aliphatic dicarboxylic acid is used as the dicarboxylic acid component, an average number of carbon atoms of the dicarboxylic acid component is preferably from 5.5 to 10.0, and more preferably from 5.6 to 8.0, of the dicarboxylic acid.

When the average number of carbon atoms of the dicarboxylic acid is 5.5 or greater, a polarizing plate having excellent durability can be obtained. When the average number of carbon atoms of the dicarboxylic acid is 10 or less, the miscibility with the resultant cellulose acylate is excellent so that occurrence of the bleeding in film production process of the cellulose acylate film can be suppressed excellently.

Examples of the aromatic dicarboxylic acid which is used for the synthesis of the polycondensation ester-based plasticizer include phthalic acid, terephthalic acid, isophthalic acid, 1,5-naphthalenedicarboxylic acid, 1,4-naphthalenedicarboxylic acid, 1,8-naphthalenedicarboxylic acid, 2,8-naphthalenedicarboxylic acid, and 2,6-naphthalenedicarboxylic acid. Of these aromatic dicarboxylic acids, phthalic acid, terephthalic acid and 2,6-naphthalenedicarboxylic acid are preferred, phthalic acid and terephthalic acid are more preferred, and terephthalic acid is still more preferred.

In the polycondensation ester derived from the diol compound, the dicarboxylic acid including the aliphatic dicarboxylic acid, the aliphatic dicarboxylic acid residue is formed.

Examples of the aliphatic dicarboxylic acid which is used for synthesis of the polycondensation ester-based plasticizer include oxalic acid, malonic acid, succinic acid, maleic acid, fumaric acid, glutaric acid, adipic acid, pimelic acid, suberic acid, azelaic acid, sebacic acid, dodecanedicarboxylic acid, and 1,4-cyclohexanedicarboxylic acid.

The diol which is used for the synthesis of the polycondensation ester-based plasticizer include an aromatic diol and an aliphatic diol. In the present invention, the polycondensation ester-based plasticizer is preferably synthesized by using at least the aliphatic diol.

The polycondensation ester-based plasticizer preferably contains an aliphatic diol residue having an average number of carbon atoms from 2.5 to 7.0, and more preferably contains an aliphatic diol residue having an average number of carbon atoms from 2.5 or 4.0.

When the average number of carbon atoms of the aliphatic diol residue is 7.0 or less, miscibility with a cellulose acylate is improved, the bleeding hardly occurs, the loss on heating of the compound hardly increases, and occurrence of surface state failure which is considered to be caused by process contamination due to drying of a cellulose acylate web can be prevented, which are excellent. Also, when the average number of carbon atoms of the aliphatic diol residue is 2.5 or greater, the synthesis is readily.

As the aliphatic diol to be used for synthesizing the polycondensation ester-based plasticizer, alkyl diols or alicyclic diols are preferred. For example, the polycondensation ester-based plasticizer can be preferably synthesized from at least one diol of ethylene glycol, 1,2-propanediol, and 1,3-propanediol, and particularly preferably at least one diol of ethylene glycol or 1,2-propanediol.

The terminal of the polycondensation ester-based plasticizer may be the diol or carboxylic acid as it is without being sealed (that is, the terminal of the polymer chain is —OH or —$CO_2H$), or sealing of the terminal may be conducted upon further reaction with a monocarboxylic acid or a monoalcohol. When the terminal of the polycondensation ester-based plasticizer is sealed, it is possible to obtain an effect that the state at an ordinary temperature is hardly changed to a solid form, which results in good handling, and a cellulose acylate film having excellent humidity stability and capable of giving polarizing plate durability can be obtained.

As for the polycondensation ester-based plasticizer, J-1 to J-38, which are described in paragraphs [0062] to [0064] of JP-A-2012-234159, are preferred.

Further, the following polycondensation ester-based plasticizers other than the above compounds may be also preferably used.

| | Dicarboxylic acid | | | Diol | | | |
|---|---|---|---|---|---|---|---|
| No. | Aromatic dicarboxylic acid (dc1) | Aliphatic dicarboxylic acid (dc2) | Dicarboxylic acid mol % ratio (dc1/dc2) | Diol 1 (do1) | Diol 2 (do2) | Diol mol % ratio (do1/do2) | Terminal |
| J-40 | PA | AA | 25/75 | ED | — | 100/0 | Acetyl ester group |
| J-41 | PA | AA | 50/50 | ED | — | 100/0 | Acetyl ester group |
| J-42 | PA | — | 100/0 | ED | — | 100/0 | Acetyl ester group |
| J-43 | — | AA | 0/100 | ED | PD | 70/30 | Acetyl ester group |
| J-44 | — | AA | 0/100 | ED | PD | 50/50 | Acetyl ester group |

In the above table, "PA" represents phthalic acid, "AA" represents adipic acid, "ED" represents ethanediol, and "PD" represents propanediol.

(Polyvalent Alcohol Ester-Based Plasticizer)

The polyvalent alcohol ester-based plasticizer to be used in the present invention is an ester which is derived from a polyvalent alcohol whose alcohol moiety has two or more hydroxy groups. As for the alcohol in the alcohol moiety, an alcohol in which a saturated carbon hydride which may be derided through an ether bond other than a hydroxy group is substituted with two or more hydroxy groups is preferred.

A polyvalent alcohol that is a synthetic raw material for the polyvalent alcohol ester-based plasticizer is represented by formula (c).

 Formula (c)

In formula (c), Rα represents a m-valent organic group, and m represents a positive integer of 2 or greater.

The number of carbon atoms of the polyvalent alcohol is preferably 5 or more, and more preferably from 5 to 20.

Such a polyvalent alcohol includes sugar alcohols and glycols.

Specifically, triethylene glycol, tetraethylene glycol, dipropylene glycol, tripropylene glycol, sorbitol, trimethylol propane, and xylitol are preferred.

The monocarboxylic acid (an acyl moiety in the ester) to be used for the polyvalent alcohol ester is an acid moiety derived from a monocarboxylic acid, and examples of such an acid include aliphatic monocarboxylic acids, alicyclic monocarboxylic acids, and aromatic monocarboxylic acids. When the alicyclic monocarboxylic acid or the aromatic monocarboxylic acid is used, it is preferable from the viewpoint of improving water-vapor transmission property and reservation property.

The aliphatic monocarboxylic acid is preferably having from 1 to 32 carbon atoms, more preferably from 1 to 20, and particularly preferably from 1 to 10. Incorporation of acetic acid is preferable because miscibility with a cellulose derivative is increased. It is also preferable that acetic acid and another monocarboxylic acid are mixed to use them.

Preferable examples of the above-described aliphatic monocarboxylic acid include: saturated fatty acids, such as acetic acid, propionic acid, butyric acid, valeric acid, caproic acid, enanthic acid, caprylic acid, pelargonic acid, capric acid, 2-ethyl-hexane carboxylic acid, undecylic acid, lauric acid, tridecylic acid, myristic acid, pentadecylic acid, palmitic acid, heptadecylic acid, stearic acid, nonadecanoic acid, arachidic acid, behenic acid, rigniceric acid, cerotic acid, heptacosanic acid, montanic acid, melisic acid, and lacceric acid; and unsaturated fatty acids, such as undecylenic acid, oleic acid, sorbic acid, linolic acid, linolenic acid, and arachidonic acid.

Preferable examples of the above-described alicyclic monocarboxylic acid include cyclopentane carboxylic acid, cyclohexane carboxylic acid, cyclooctane carboxylic acid, and their derivatives.

Preferable examples of the above-described aromatic monocarboxylic acid include: benzoic acid; benzoic acids, such as toluic acid, in which an alkyl group is introduced into the benzene ring of benzoic acid; aromatic monocarboxylic acids having two or more benzene rings, such as biphenyl carboxylic acid, naphthalene carboxylic acid, and tetralin carboxylic acid; and their derivatives. Especially, benzoic acid is preferred.

Although the molecular weight of the polyvalent alcohol ester-based plasticizer is not particularly limited, the molecular weight is preferably from 300 to 3,000, and more preferably from 350 to 1,500. Setting of the molecular weight at a larger value is preferable because volatilization from the optical film is excellently suppressed. On the other hand, setting of the molecular weight at a smaller value is preferable, from the viewpoints of moisture-vapor permeability and miscibility with cellulose derivatives.

As for the polyvalent alcohol ester-based plasticizer, preferred are compounds described in, for example, paragraphs [0045] to [0049] of JP-A-2012-234159, which is hereby preferably incorporated by reference.

(Carbohydrate Derivative-Based Plasticizer)

As the carbohydrate derivative-based plasticizer, derivatives of carbohydrates including monosaccharides or from 2 to 10 monosaccharide units are preferred. Among those, the acylated ones are more preferred.

Preferable examples of the carbohydrates including the above-described monosaccharides or from 2 to 10 monosaccharide units include: ribose, arabinose, xylose, lyxose, glucose, fructose, mannose, galactose, trehalose, maltose, cellobiose, lactose, sucrose, sucralose, α-cyclodextrin, β-cyclodextrin, γ-cyclodextrin, δ-cyclodextrin, xylitol, and sorbitol. More preferred examples of the same include: arabinose, xylose, glucose, fructose, mannose, galactose, maltose, cellobiose, sucrose, β-cyclodextrin, and γ-cyclodextrin. Particularly preferred examples include: xylose, glucose, fructose, mannose, galactose, maltose, cellobiose, sucrose, xylitol, and sorbitol.

Preferred examples of the carbohydrate derivative-based plasticizer include: maltose octaacetate, cellobiose octaacetate, sucrose octaacetate, xylose tetrapropionate, glucose pentapropionate, fructose pentapropionate, mannose pentapropionate, galactose pentapropionate, maltose octapropionate, cellobiose octapropionate, sucrose octapropionate, xylose tetrabenzoate, glucose pentabenzoate, fructose pentabenzoate, mannose pentabenzoate, galactose pentabenzoate, maltose octabenzoate, cellobiose octabenzoate, sucrose octabenzoate, xylitol pentabenzoate, and sorbitol hexabenzoate.

The carbohydrate derivative-based plasticizer preferably has a pyranose structure or a furanose structure.

As for the carbohydrate derivative-based plasticizer, compounds described in paragraphs [0030] to [0039] of JP-A-2012-234159 are preferred.

Note that, in the present invention, the content described in paragraphs [0026] to [0068] of JP-A-2012-234159 is preferably applied to the plasticizer, which is hereby preferably incorporated by reference.

The content of the plasticizer is preferably from 1 to 20% by mass, with respect to the cellulose acylate. When the content is 1% by mass or greater, an effect of improvement in polarizing plate durability can be easily achieved. While, on the other hand, when the content is 20% by mass or less, bleeding is suppressed. The content is more preferably from 2 to 15% by mass, and particularly preferably from 5 to 15% by mass. Note that two or more plasticizers may be added. When the two or more plasticizers are added, a specific example of the addition amount and a preferred range thereof are the same as described above.

The timing of addition of the plasticizers to the cellulose acylate film is not particularly limited, as long as it is added at the time of film production. For example, it may be added at the time when the cellulose acylate is synthesized, or alternatively it may be mixed with the cellulose acylate at the time of preparing a dope.

(Antioxidant)

The optical film of the present invention preferably contains an antioxidant. In the present invention, it is possible to add to a cellulose acylate solution an antioxidant, In the present invention, it is possible to add any of antioxidants, for example, a phenol-based or hydroquinone-based antioxidant, such as 2,6-di-tert-butyl-4-methylphenol, 4,4'-thio-bis-(6-tert-butyl-3-methylphenol), 1,1'-bis(4-hydroxyphenyl)cyclohexane, 2,2'-methylene-bis(4-ethyl-6-tert-butylphenol), 2,5-di-tert-butylhydroquinone, and pentaerythrityl-tetrakis[3-(3,5-di-tert-butyl-4-hydroxyphenyl)propionate]. Further, it is preferable to add a phosphorus-based antioxidant, such as tris(4-methoxy-3,5-diphenyl) phosphite, tris(nonylphenyl)phosphite, tris(2,4-di-tert-butylphenyl)phosphite, bis(2,6-di-tert-butyl-4-methylphenyl)pentaerythritol diphosphite, and bis(2,4-di-tert- butylphenyl)pentaerythritol diphosphite.

As for the content of the antioxidant, the antioxidant is preferably added in the proportion of from 0.001 to 5.0 parts by mass, more preferably in the proportion of from 0.01 to 5.0 parts by mass, with respect to 100 parts by mass of the cellulose acylate.

(Radical Scavenger)

The optical film of the present invention preferably contains a radical scavenger. An HALS (hindered amine-based light stabilizer) and a reductone are preferably used as the radical scavenger.

The HALS is particularly preferably a compound having a 2,2,6,6-tetramethyl-piperidine ring, it is preferably a compound in which the 1-position of piperidine is a hydrogen atom, an alkyl group, an alkoxy group, a hydroxy group, an oxy radical group (—O.), an acyloxy group, or an acyl group, and it is more preferably a compound in which the 4-position thereof is a hydrogen atom, a hydroxy group, an acyloxy group, an amino group which may have a substituent, an alkoxy group, or an aryloxy group. In addition, it is also preferably a compound having from two to five 2,2,6,6-tetramethyl-piperidine rings in the molecule.

Examples of such a compound include Sunlizer HA-622 (trade name, manufactured by Sort K.K.); CHIMASSORB 2020FDL, TINUVIN 770DF, TINUVIN 152, TINUVIN 123, and FLAMESTAB NOR 116 FF (each trade name, manufactured by BASF Japan Ltd. (former Chiba Specialty Chemicals)); CYASORB UV-3346 and CYASORB UV-3529 (each trade name, manufactured by SUN CHEMICAL COMPANY LTD.).

Examples of the reductone include compounds exemplified in JP-A-6-27599, paragraph Nos. [0014] to [0034]; compounds exemplified in JP-A-6-110163, paragraph Nos. [0012] to [0020]; and compounds exemplified in JP-A-8-114899, paragraph Nos. [0022] to [0031].

In addition, it is possible to preferably use an oil-solubilized derivative of ascorbic acid and erythorbic acid, and examples include L-ascorbyl stearate, L-ascorbyl tetraisopalmitate, L-ascorbyl palmitate, erythorbyl palmitate, and erythorbyl tetraisopalmitate. Among them, those having an ascorbic acid skeleton are preferable, and myristate, palmitate, and stearate of L-ascorbic acid are particularly preferable.

The content of the radical scavenger in the cellulose acylate film is preferably from 0.001 to 2.0 parts by mass, and more preferably from 0.01 to 1.0 part by mass, with respect to 100 parts by mass of the cellulose acylate.

(Other Degradation Inhibitor)

As the other degradation inhibitor for the cellulose acylate, it is possible to use an additive which is known as a peroxide decomposer, a radical inhibitor, or a metal deactivator. Examples thereof include compounds described in JP-A-2006-251746, paragraph Nos. [0074] to [0081] and [0082] to [0117].

The above-described radical scavenger also exhibits anti-deteriorating effects. Amines are also known as a degradation inhibitor. Examples thereof include compounds described in paragraphs [0009] to [0080] of JP-A-5-194789, and aliphatic amines, such as tri-n-octylamine, tri-isooctylamine, tris(2-ethylhexyl)amine, and N,N-dimethyldodecylamine.

Further, polyvalent amines having two or more amino groups are also preferably used. As for the polyvalent amines, those having two or more primary or secondary amino groups are preferred. Examples of the compound having two or more amino groups include nitrogen-containing heterocyclic compounds (compounds having a pyrazolidine ring, a piperazine ring, or the like), and polyamine-based compounds (chain-like or ring-like polyamines, for example, diethylene triamine, tetraethylene pentamine, N,N'-bis(aminoethyl)-1,3-propanediamine, N,N,N',N'',N'''-pentakis(2-hydroxypropyl)diethylene triamine, polyethyleneimine, modified polyethyleneimine, and a compound containing cyclam as a basic skeleton).

The content of the degradation inhibitor in the cellulose acylate film is preferably from 1 ppm to 10%, more preferably from 1 ppm to 5.0%, still more preferably from 10 ppm to 1.0%, in terms of mass proportion.

(Ultraviolet Absorber)

The optical film of the present invention may contain an ultraviolet absorber, from the viewpoint of preventing deterioration of a polarizing plate, a liquid crystal or the like. The ultraviolet absorber may be added to the cellulose acylate solution. In the present invention, as the ultraviolet absorber, it is preferable to use those which have excellent absorption capacity of ultraviolet rays at the wavelength of 370 nm or less and which exhibit a low absorption of visible light having the wavelength of 400 nm or longer, from the viewpoint of good property for the liquid crystal display. Examples of the ultraviolet absorber which is preferably used in the present invention include: a hindered phenol-based compound, a hydroxybenzophenone-based compound, a benzotriazole-based compound, a salicylic acid ester-based compound, a benzophenone-based compound, a cyano acrylate-based compound, and a nickel complex-based compound.

The hindered phenol-based compound is not particularly limited, but preferred examples of the hindered phenol-based compound include at least one selected from among 2,6-di-tert-butyl-p-cresol, pentaerythrityl-tetrakis[3-(3,5-di-tert-butyl-4-hydroxyphenyl)propionate], N,N'-hexamethylene-bis(3,5-di-tert-butyl-4-hydroxy-hydrocinnamide), 1,3,5-trimethyl-2,4,6-tris(3,5-di-tert-butyl-4-hydroxybenzyl)benzene, and tris(3,5-di-tert-butyl-4-hydroxybenzyeisocyanurate.

The benzotriazole-based compound is not particularly limited, but preferred examples of the benzotriazole-based compound include at least one selected from among 2-(2'-hydroxy-5'-methylphenyl)benzotriazole, 2,2-methylene-bis[4-(1,1,3,3-tetramethylbutyl)-6-(2H-benzotriazole-2-yl)phenol], (2,4-bis-(n-octylthio)-6-(4-hydroxy-3,5-di-tert-butylanilino)-1,3,5-triazine, triethyleneglycol-bis[3-(3-tert-butyl-5-methyl-4-hydroxyphenyl)propionate], N,N'-hexamethylene-bis(3,5-di-tert-butyl-4-hydroxy-hydrocinnamide), 1,3,5-trimethyl-2,4,6-tris(3,5-di-tert-butyl-4-hydroxybenzyl)benzene, 2-(2'-hydroxy-3',5'-di-tert-butylphenyl)-5-chlorobenzotriazole, 2-(2'-hydroxy-3',5'-di-tert-amylphenyl)-5-chlorobenzotriazole, 2,6-di -tert-butyl-p-cresol, pentaerythrityl-tetrakis[3-(3,5-di-tert-butyl-4-hydroxyphenyl)propionate], 2-(3,5-di-tert-amyl-2-hydroxyphenyl)benzotriazole, and 2-(2H-benzotriazole-2-yl)-6-(1-methyl-1-phenylethyl)-4-(1,1,3,3-tetramethylbutyl)phenole.

As for these compounds, TINUVINs, such as TINUVIN 99-2, TINUVIN 109, TINUVIN 171, TINUVIN 320, TINUVIN 326, TINUVIN 327, TINUVIN 328, TINUVIN 329, TINUVIN 343, TINUVIN 900, TINUVIN 928, TINUVIN P, and TINUVIN PS, are available as a marketed product. Each of them is a product of BASF and can be preferably used.

The addition amount of the ultraviolet absorber is preferably from 1 ppm to 10%, and more preferably from 1 ppm to 5.0%, and still more preferably 10 ppm to 5.0%, in terms of mass proportion in the entire cellulose acylate film.

(Peeling Agent)

Any peeling agent may be added to the cellulose acylate film of the present invention.

The peeling agent is preferably an organic acid, a polyvalent carboxylic acid derivative, a surfactant, or a chelating agent. For example, compounds described in JP-A-2006-45497, paragraph Nos. [0048] to [0081], compounds described in JP-A-2002-322294, paragraph Nos. [0077] to [0086], compounds described in JP-A-2012-72348, paragraph Nos. [0030] to [0056], can be preferably used. The content of the peeling agent in the cellulose acylate film is preferably from 1 ppm to 5.0%, more preferably from 1 ppm to 2.0%, in terms of mass proportion.

The organic acid includes compounds described in paragraphs [0079] to [0082] of JP-A-2002-3222294. Examples thereof include citric acid, oxalic acid, adipic acid, succinic acid, malic acid, and tartaric acid.

Further as for the organic acid, amino acids are also preferred. Examples thereof include asparagine, asparaginic acid, adenine, alanine, β-alanine, arginine, isoleucine, glycine, glutamine, glutamic acid, serine, tyrosine, tryptophan, threonine, norleucine, valine, phenylalanine, methionine, rycin, and leucine.

The organic acid includes its alkali metal salts, its alkali-earth metal salts, and its heavy metal salts including transition metals, although it may be also used as a free acid. Among metals of the each salt, as for the alkali metal, lithium, potassium, sodium, and the like are exemplified, and as for the alkali-earth metal, calcium, magnesium, barium, strontium and the like are exemplified. As for the heavy metal including a transition metal, aluminum, zinc, tin, nickel, iron, lead, copper, silver and the like are exemplified. Further, salts of substituted or unsubstituted amines having carbon atoms of 5 or less are also preferred. As for the amine of the salt, ammonium, methylamine, ethylamine, propylamine, butylamine, dimethylamine, trimethylamine, triethylamine, hydroxyethylamine, bis(hydroxyethyl)amine, tris(hydroxyethyl)amine and the like are exemplified. Preferred metals are sodium for the alkali metal, and calcium and magnesium for the alkali-earth metal. These alkali metals and alkali-earth metals may be used respectively singly or in combination of two or more metals, and further the alkali metal and the alkali-earth metal may be used in combination.

As for the polyvalent carboxylic acid derivative, ester compounds and amide compounds are preferred.

The carboxylic acid component is a polyvalent carboxylic acid, and although the carboxylic acid may be any of aliphatic or aromatic carboxylic acids, an aliphatic carboxylic acid is preferred. The aliphatic carboxylic acid may be a saturated or unsaturated, straight-chain, branched-chain or cyclic aliphatic carboxylic acid, and may have a substituent. The substituent includes an alkyl group, an alkenyl group, an aryl group, a hydroxy group, an amino group, an alkoxy group, an alkenyloxy group, an acyloxy group, and an acylamino group.

The aromatic carboxylic acid includes phthalic acid, terephthalic acid, isophthalic acid, 1,3,5-benzenetricarboxylic acid, and the like. The aliphatic carboxylic acid includes oxalic acid, malonic acid, succinic acid, glutaric acid, adipic acid, and sebacic acid. The carboxylic acid having a substituent includes malic acid, citric acid and tartaric acid.

As for the polyvalent carboxylic acid ester, the alcohol component: the group which binds to the oxygen atom derived from the ester functional group: —C(=O)—O— is preferably a substituted or unsubstituted alkyl group [for example, methyl, ethyl, isopropyl, t-butyl, 2-ethylhexyl, —CH$_2$CH$_2$O—(CH$_2$CH$_2$)n-C$_2$H$_5$], and an alkenyl group (for example, vinyl, allyl, 2-methyl-2-propenyl, 2-butenyl, oleyl). The total number of carbon atoms of the alcohol component (the group which binds to the oxygen atom) is preferably from 1 to 200, more preferably from 1 to 100, and still more preferably from 1 to 50. As for the substituent which the alkyl group and the alkenyl group may have, an alkoxy group, an alkenyloxy group, a hydroxy group, and an acyloxy group are preferred, and an alkoxy group is more preferred. The alkoxy group and the alkenyloxy group preferably each contain a (poly)oxyalkylene group. In particular, the (poly)oxyalkylene group is preferably a (poly)oxyethylene group, a (poly)oxypropylene group, and a (poly)oxybutylene group.

Further, an alcohol which is a raw material for the alcohol component may be monovalent or polyvalent. Examples of the polyvalent alcohol include ethylene glycol, propylene glycol, glycerin, and pentaerythritol. Those compounds whose hydroxy group moiety (—OH) is modified to a (poly)oxyalkylenoxy group [for example, —(OCH$_2$CH$_2$)n-OH, —(OC$_3$H$_6$)$_n$OH] are also preferred.

As for the polyvalent carboxylic acid amide, an amine compound which is the amine component thereof may be a primary amine or a secondary amine, and it is not particularly limited. The substituent, by which the nitrogen atom derived from the amide functional group: —C(=O)—N< is substituted, is preferably an alkyl group [for example, methyl, ethyl, isopropyl, t-butyl, 2-ethylhexyl, —CH$_2$CH$_2$O—(CH$_2$CH$_2$)n-C$_2$H$_5$], and an alkenyl group (for example, vinyl, allyl, 2-methyl-2-propenyl, 2-butenyl). The total number of carbon atoms of an amine compound which is the amine component is preferably from 1 to 200, more preferably from 1 to 100, and still more preferably from 1 to 50. As for the substituent which the alkyl group and the alkenyl group may have, an alkoxy group, an alkenyloxy group, a hydroxy group, an acyloxy group, an amino group, and an acylamino group are preferred, and an alkoxy group is more preferred. The alkoxy group and the alkenyloxy group preferably each contain a (poly)oxyalkylene group. In particular, the (poly)oxyalkylene group is preferably a (poly)oxyethylene group, a (poly)oxypropylene group, and a (poly)oxybutylene group. Further, it is also preferred that the foregoing (poly)oxyalkylene partial structure contains a branched (poly)oxyalkylene group through glycerin.

An amine compound which is a raw material for the amine component may be monovalent or polyvalent.

Among the polyvalent carboxylic acid derivatives, an organic acid monoglyceride having an unreacted and releasable carboxyl group is particularly preferred. Examples of the marketed products thereof include POEM K37-V (glycerin citrate/oleate ester) manufactured by Riken Vitamin Co., Ltd., and STEP SS (glycerin stearate/palmitate/succinate ester) manufactured by Kao Corporation.

As for the above-described surfactant, compounds described in paragraphs [0050] to [0051] of JP-A-2006-45497, and compounds described in paragraphs [0127] to [0128] of JP-A-2002-322294 may be preferably used. Specifically the nonionic surfactant includes polyoxyethylene alkyl ether, polyoxyethylene alkyl phenyl ether, polyoxyethylene/polyoxypropylene glycol, polyvalent alcohol aliphatic acid partial ester, polyoxyethylene polyvalent alcohol aliphatic acid partial ester, polyoxyethylene aliphatic acid ester, polyglycerin aliphatic acid ester, aliphatic acid diethanolamide, triethanolamine aliphatic acid partial ester, and polyether amine. Further, the marketed product thereof includes NYMEEN L-202, STAFOAM DO, and STAFOAM DL (each trade names, manufactured by NOF CORPORATION).

The above-described chelating agent is a compound which is able to coordinate (chelate) to a multivalent metal ion, such as a metal ion like an iron ion, and an alkaline-earth metal ion like a calcium ion. Any of various chelating agents which are represented by aminopolycarboxylic acids, aminopolyphospholic acids, alkylphospholic acids, and phsphonocarboxylic acids may be used. As for the chelating agent, compounds described in JP-B-6-8956, JP-A-11-190892, JP-A-2000-18038, JP-A-2010-158640, JP-A-2006-328203, JP-A-2005-68246, and JP-A-2006-306969 may be used.

Specifically, examples thereof include ethylenediamine tetraacetic acid, hydroxyethyl ethylenediamine triacetic acid, diethylenetriamine pentaacetic acid, nitrilo triacetic acid, triethylenetetramine hexaacetic acid, cyclohexanediamine tetraacetic acid, hydroxyethylimino diacetic acid, ethyleneglycol bis(2-aminoethyl ether)tetraacetic acid, 1,3-diaminopropane tetraacetic acid, phosphonic acid, 1-hydroxyethylethylidene-1,1-diphosphonic acid, nitrilo -N,N,N-trimethylene phosphonic acid, ethylenediamine-N,N,N,N-tetramethylene phosphonic acid, ethylenediamine-di(o-hydroxyphenylacetic acid), DL-alanine-N,N-diacetic acid, aspartic acid-N,N-diacetic acid, glutamic acid-N,N-diacetic acid, serine-N,N-diacetic acid, polyacrylic acid, an isoamylene/maleic acid copolymer, an acrylic acid/maleic acid copolymer, an acrylic acid/methacrylic acid copolymer, silicic acid, gluconic acid, hydroxybenzylimino diacetic acid, and imino diacetic acid. Further, an oil-soluble chelating agent is also preferably used. As for the marketed product thereof, Techrun DO (trade name, manufactured by Nagase ChemteX Corporation), CHELEST MZ-2 and CHELEST MZ-8 (each trade name, manufactured by Chelest Corporation) may be used.

(Matting Agent)

A matting agent may be added to the optical film of the present invention, from the viewpoint of film lubricity (slipping property) and stable production of the film. The matting agent may be either a matting agent composed of an inorganic compound or a matting agent composed of an organic compound.

Preferable examples of the matting agent composed of the inorganic compound include silicon-containing inorganic compounds (e.g., silicon dioxide, calcined calcium silicate, hydrated calcium silicate, aluminum silicate, magnesium silicate), titanium oxide, zinc oxide, aluminum oxide, barium oxide, zirconium oxide, strontium oxide, antimony oxide, tin oxide, tin-antimony oxide, calcium carbonate, talc, clay, calcined kaolin, and calcium phosphate. Further, silicon-containing inorganic compounds and zirconium oxide are more preferred. Silicon dioxide is particularly preferred because it is capable of lowering haze of the cellulose acylate film.

As fine particles of silicon dioxide, for example, commercial products which have trade names, such as Aerosil R972, R974, R812, 200, 300, 8202, OX50, TT600 (all manufactured by Nippon Aerosil) are usable. As fine particles of zirconium oxide, for example, commercial products which have trade names, such as Aerosil R976 and R811 (both manufactured by Nippon Aerosil) are usable.

Preferable examples of the matting agent composed of the organic compound include polymers, such as silicone resins, fluororesins, acrylic resins, and the like. Above all, silicone resins are more preferred. Of the silicone resins, those having a three-dimensional network structure are particularly preferred. For example, it is possible to use commercially available products having trade names, such as Tospearl 103, Tospearl 105, Tospearl 108, Tospearl 120, Tospearl 145, Tospearl 3120, and Tospearl 240 (all manufactured by Toshiba Silicone Co., Ltd.).

When the matting agent is added to the cellulose acylate solution, any method may be used with no problem, as long as a desired cellulose acylate solution can be obtained by the any method. For example, the additive may be added in the stage where a cellulose acylate is mixed with a solvent; or after preparing a mixture solution from a cellulose acylate and a solvent, the additive may be added thereto.

Further, the additive may be added to and mixed with a dope just before casting of the dope. This is what is called "just before" addition method, and the mixing is conducted by screw kneading provided on-line. Specifically, a static mixer like an in-line mixer is preferred. As the in-line mixer, for example, a static mixer, SWJ (Toray's static intratubular mixer, Hi-Mixer, manufactured by Toray Engineering Co., Ltd.) is preferred.

Regarding the in-line addition, JP-A-2003-053752 describes a method for producing a cellulose acylate film in which, for the purpose of preventing concentration unevenness and particle aggregation, the distance L between a nozzle tip through which an additive liquid having a composition different from that of a main raw material dope is added and a start end of the in-line mixer is controlled to be at most 5 times the inner diameter d of the main raw material-feeding pipe, thereby preventing concentration unevenness and aggregation of matting particles and the like. JP-A-2003-053752 discloses a more preferred embodiment, in which the distance (L) between the nozzle tip opening through which the additive liquid having a composition different from that of the main raw material dope is added and the start end of the in-line mixer is controlled to be at most 10 times the inner diameter (d) of the feeding nozzle tip opening, and the in-line mixer is a static non-stirring intratubular mixer or a dynamic stirring intratubular mixer. More specifically, JP-A-2003-053752 discloses that the flow rate of the cellulose acylate film main raw material dope/in-line additive liquid is from 10/1 to 500/1, and preferably from 50/1 to 200/1. JP-A-2003-014933 discloses a method of providing a phase difference film which is free from a trouble of additive bleeding and a trouble of interlayer peeling and which has good lubricity and excellent transparency; and regarding the method of adding additives to the film, JP-A-2003-014933 discloses that the additive may be added to a dissolving tank, or the additive or a solution or dispersion of the additive or an additive-dissolved- or dispersed liquid may be added to the dope in a dissolving tank or solution sending in the process of from the dissolving tank to a co-casting die, and further discloses that in the latter case, a mixing means, such as a static mixer, is preferably provided therein for the purpose of enhancing the mixing efficiency.

The addition amount of the matting agent is particularly preferably from 0.05 to 1.0 mass %, in terms of mass proportion in the entire cellulose acylate film. Thus, the matting agent does not increase haze of the cellulose acylate film. In fact, when the film containing a suitable amount of a matting agent is used in LCD, the film contributes to being free from disadvantages of contract lowering and bright spot formation. In addition to those, the matting agent in the film can realize scratch resistance of the film. From these viewpoints of those, the matting agent is preferably incorporated in the proportion of from 0.05 to 1.0% by mass with respect to the cellulose acylate.

<Physical Properties of Cellulose Acylate Film>
(Hardness)

With regard to the surface hardness, the Knoop hardness by the Knoop method using a Knoop indenter is high and the pencil hardness is also favorable. The Knoop hardness can be measured by a hardness tester with a Knoop indenter as the indenter, for example, the "FISCHERSCOPE H100Vp-type hardness tester" manufactured by Fischer Instruments K. K.

The pencil hardness can be evaluated, for example, by the pencil hardness evaluation method regulated in JIS K5400 using a test pencil regulated in JIS 56006.
(Elastic Modulus (Tensile Elastic Modulus))

The cellulose acylate film of the present invention exhibits practically-sufficient elastic modulus (tensile elastic modulus). The range of the elastic modulus, although it is not particularly limited, is preferably from 1.0 GPa to 7.0 GPa, and more preferably from 2.0 GPa to 6.5 GPa, from the viewpoint of production suitability and handling property. The compound represented by any of formula (I) to (III) according to the present invention act such that the cellulose acylate film is hydrophobized by addition of the compound to a cellulose acylate film, thereby improving elastic modulus. In this point, the present invention also has an advantage.
(Photoelastic Coefficient)

The absolute value of photoelastic coefficient of the cellulose acylate film of the present invention is preferably $8.0 \times 10^{-12}$ $m^2/N$ or less, more preferably $6.0 \times 10^{-12}$ $m^2/N$ or less, and still more preferably $5.0 \times 10^{-12}$ $m^2/N$ or less. Lessening the photoelastic coefficient of the cellulose acylate film enables suppression of occurrence of unevenness under the conditions of high temperature and high humidity upon mounting of the optical film of the present invention including the cellulose acylate film into a liquid crystal display as a polarizing plate protective film. The photoelastic coefficient is measured and calculated in accordance with the following method, unless specified otherwise.

The lower limit of the photoelastic coefficient is not particularly limited, but it is practical to be $0.1 \times 10^{-12}$ $m^2/N$ or more.

A cellulose acylate film is cut into a specimen of 3.5 cm×12 cm and Re is measured under each load of non-load, 250 g, 500 g, 1,000 g and 1,500 g, using an ellipsometer (M 150 [trade name], manufactured by JASCO Corporation), and by the slope of a straight line of Re change to stress, the photoelastic coefficient is calculated.
(Moisture Content)

The moisture content of the cellulose acylate film can be evaluated by measurement of equilibrium moisture content under the constant temperature and humidity. The equilibrium moisture content is obtained by the following method. That is, the moisture content of a sample which has reached equilibrium after leaving it for 24 hours at the below temperature and humidity is measured in accordance with Karl Fischer method, and the obtained moisture content (g) is divided by the sample mass (g) to obtain the equilibrium moisture content.

The moisture content of the cellulose acylate film of the present invention under the conditions of 25° C. and relative humidity of 80% is preferably 5% by mass or less, more preferably 4% by mass or less, and still more preferably less than 3% by mass. Lessening the moisture content of the cellulose acylate film enables suppression of occurrence of display unevenness of a liquid crystal display, under the conditions of high temperature and high humidity, upon mounting of the optical film of the present invention including the cellulose acylate film into the liquid crystal display as a polarizing plate protective film. The lower limit of the moisture content is not particularly limited, but it is practical to be 0.1% by mass or greater.

(Water-Vapor Transmission Ratio)

The water-vapor transmission ratio of the cellulose acylate film can be measured and evaluated by the following method. That is, the mass of water-vapor which passes through the sample for 24 hours in the atmosphere of temperature: 40° C. and relative humidity: 90% is measured in accordance with the water-vapor transmission ratio test (cup method) prescribed in JIS Z0208, and the thus-obtained value is converted to a value passing through the sample for 24 hours per m$^2$ of the sample area, to evaluate the water-vapor transmission ratio.

The water-vapor transmission ratio of the cellulose acylate film of the present invention is preferably from 500 to 2,000 g/m$^2$·day, more preferably from 900 to 1,300 g/m$^2$·day.

(Haze)

The cellulose acylate film preferably has a haze of 1% or less, more preferably 0.7% or less, even more preferably 0.5% or less. When the haze is lowered to the above-described upper limit or less, the cellulose acylate film has advantages in that transparency of the film is more increased and thus the film becomes more usable as an optical film. The haze is measured and calculated in accordance with the method as described below, unless specified otherwise. The lower limit of the haze is not particularly limited, but it is practical to be 0.001% or greater.

Haze of the cellulose acylate film specimens of 40 mm×80 mm in size is measured in an environment at 25° C. and 60% relative humidity, using a haze meter (HGM-2DP, from Suga Test Instruments Co., Ltd.), according to JIS K7136.

(Film Thickness)

The average film thickness of the cellulose acylate film is preferably from 5 to 100 μm, more preferably from 5 to 80 μm, and still more preferably from 5 to 80 μm. Setting the average film thickness to 5 μm or greater is preferable, because handling property in production of a web film is improved. While, on the other hand, when the average film thickness is set to 80 μm or less, the response to humidity change becomes easy and thus maintenance of the optical characteristics becomes easy.

Further, in the case where the cellulose acylate film has a multi-layered structure of three or more multi-layers, the film thickness of the core layer is preferably from 3 to 70 μm, and more preferably from 5 to 60 μm, and each of the film thicknesses of the skin layer A and skin layer B is more preferably from 0.5 to 20 μm, particularly preferably from 0.5 to 10 μm, and most preferably from 0.5 to 3 μm.

(Width)

The film width of the cellulose acylate film is preferably from 700 to 3,000 mm, more preferably from 1,000 to 2,800 mm, and particularly preferably from 1,300 to 2,500 mm.

<Production Method of Cellulose Acylate Film>

The production method of the cellulose acylate film of the present invention is not particularly limited, but the cellulose acylate film is preferably produced by the melt film forming method or the solution film forming method. The production by the solution film forming method (i.e. a solvent-casting method) is more preferable. Examples of production of cellulose acylate film using a solvent-casting method are given in U.S. Pat. Nos. 2,336,310, 2,367,603, 2,492,078, 2,492,977, 2,492,978, 2,607,704, 2,739,069, and 2,739,070, British Patents 640731 and 736892, JP-B-45-4554, JP-B-49-5614, JP-A-60-176834, JP-A-60-203430, and JP-A-62-115035, each of which is referred to. The cellulose acylate film may be stretched. Regarding the method and condition for stretching treatment, for example, referred to are JP-A-62-115035, JP-A-4-152125, JP-A-4-284211, JP-A-4-298310, and JP-A-11-48271.

(Casting Methods)

As the method of casting a solution, examples of the solution casting method (i.e. solvent-casting method) include: a method for uniformly extruding a prepared dope from a pressure die onto a metal support; a doctor blade method for adjusting, with a blade, the film thickness of a dope once cast onto a metal support; and a reverse roll coater method for adjusting it with a reverse rotating roll, but the method of using a pressure die is preferred. Examples of the pressure die include a coat hanger-type or a T die-type, and any of them may be preferably used. In addition to these methods exemplified herein, various methods of film production by casting a cellulose acylate solution, which are known in the art, may be employed. When each of conditions is set in consideration of the difference in the boiling points of solvents to be used, the same effects as the contents described in each publication can be obtained.

Co-Casting

In formation of the cellulose acylate film, a multi-layer casting method, such as a co-casting method, a sequential casting method, and a coating method, is preferable. Especially, a simultaneous co-casting method is particularly preferred, from the viewpoints of stable production and production cost reduction.

Figure 3:
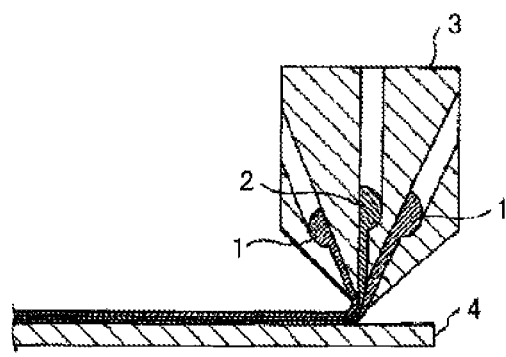
FIG. 3 is a schematic view showing an example in which casting of the cellulose acylate film having a three-layer structure is carried out by a simultaneous co-casting using a co-casting die.

In the case where the film is produced according to a co-casting method and a sequential casting method, first, a cellulose acetate solution (dope) for each layer is prepared. The co-casting method (multilayer simultaneous casting method) is a casting method in which individual layers are simultaneously cast by simultaneously extruding co-casting dopes onto a casting support (band or dram) from a casting Giesser through which the individual casting dopes for intended layers (the number of the layers may be three or more) are simultaneously extruded via different slits, and then at a suitable timing, the film thus formed on the support is peeled away and dried. In FIG. 3, the cross-sectional view shows a state in which casting is performed by simultaneously extruding three layers formed of a dope 1 for two surface layers and a dope 2 for core layer on a casting support 4, using a co-casting Giesser 3.

The sequential casting method is a casting method in which first a casting dope for first layer is extruded out and cast onto a casting support through a casting Giesser, then after it is dried or not dried, a casting dope for second layer is extruded through the casting Giesser and cast onto the first layer, and if needed, three or more layers are sequentially formed by casting and laminating dopes in the same manner as the above, and then at a suitable timing, the resultant laminate is peeled away from the support and dried to form a cellulose acylate film. The coating method is generally a method in which a core layer is formed of film by means of film formation with solution, then a coating solution for a surface layer is prepared, and then using a suitable coater, the coating solution is applied onto the core layer first on one surface thereof and next on the other surface thereof, or simultaneously on both surfaces thereof, and dried to form a multi-layered cellulose acylate film.

As the endlessly running metal support for use in production of the cellulose acylate film, it is possible to use a dram the surface of which is mirror-finished by chromium plating, or a stainless belt (may be called as a band) the surface of which is mirror-finished by surface polish. One or at least two pressure dies may be used by arranging it or them above the metal support. Preferably, one or two pressure dies are arranged. In the case where two or more pressure dies are arranged, a casting amount of the dope may be divided into portions which are suitable for the individual dies; or the casting dope may be fed to the die at a suitable proportion from a plurality of precision metering gear pumps. The temperature of the dope (resin solution) to be used for casting is preferably from −10° C. to 55° C., and more preferably from 25° C. to 50° C. In this case, the solution temperature may be the same throughout the entire process, or may be different in different stages of the process. In the case where the temperatures are different in different stages, it is no problem as long as the dope has a desired temperature just before casting.

Further, the material of the above metal support, although it is not particularly limited, is preferably made of SUS (for example, SUS 316).

(Peeling)

The method of producing the cellulose acylate film preferably includes a step of peeling off the above dope film from the metal support. In the production method of the cellulose acylate film, the method of peeling off is not particularly limited, and peeling property can be improved by any of methods known for peeling-off.

(Stretching Process)

The method of producing the cellulose acylate film preferably includes a stretching process after film production. The stretching direction of the cellulose acylate film is preferable in any of a cellulose acylate film conveying direction (MD direction) and an orthogonal direction (TD direction) to the conveying direction. However, the orthogonal direction (TD direction) to cellulose acylate film conveying direction is particularly preferred, from the viewpoint of the subsequent polarizing plate-manufacturing process using the cellulose acylate film.

A method of stretching the film in the TD direction is described, for example, in JP-A-62-115035, JP-A-4-152125, JP-A-4-284211, JP-A-4-298310, JP-A-11-48271, and the like. In the case of stretching in the MD direction, the cellulose acylate film is stretched when the cellulose acylate film winding speed is set to be faster than the cellulose acylate film peeling-off speed, for example, by adjusting a speed of the cellulose acylate film-conveying roller. In the case of stretching in the TD direction, the cellulose acylate film may be stretched by conveying the cellulose acylate film while holding the width of the cellulose acylate film with a tenter, and extending the width of the tenter gradually. After drying the cellulose acylate film, the film may be also stretched by using a stretching machine (preferably uniaxial stretching by using a long stretching machine).

In the case where the cellulose acylate film is used as a protective film for a polarizer, the transmission axis of the polarizer and the in-plane slow axis of the cellulose acylate film are required to be arranged parallel to one another, in order to suppress the light leakage when viewed from oblique directions to the polarizing plate. The transmission axis of the roll film-shaped polarizer that is produced continuously is generally parallel to the width direction of the roll film, and thus, in order to continuously sticking the above roll film-shaped polarizing element together with a protective film composed of the roll film-shaped cellulose acylate film, the in-plane slow axis of the roll film-shaped protective film is required to be parallel to the width direction of the cellulose acylate film. Accordingly, the film is preferably stretched to a larger extent in the TD direction.

The stretching treatment may be conducted in the course of the film production process, or the original film obtained by rewinding the produced film may be subjected to a stretching treatment.

The stretching in the TD direction is preferably from 5 to 100%, more preferably from 5 to 80%, and particularly preferably from 5 to 40%. Meanwhile, non-stretching means that stretching is 0%. The stretching treatment may be conducted in the course of the film production process, or the original film obtained by rewinding the produced film may be subjected to a stretching treatment. In the former case, stretching may be conducted in the condition where a certain amount of a residual solvent is contained, and when the residual solvent amount, i.e. (mass of residual volatile substance/mass of film after heat treatment)×100(%), is from 0.05 to 50%, the stretching is preferably conducted. It is particularly preferable to conduct the stretching of from 5 to 80% in the condition where the residual solvent amount is from 0.05 to 5%.

(Drying)

It is preferable, from the viewpoint of development of retardation, that the method of producing the cellulose acylate film includes a step of drying the cellulose acylate film, and a step of stretching the thus-dried cellulose acylate film at a temperature which is equal to or higher than the glass transition temperature (Tg)−10° C.

Drying of the dope provided on the metal support that is included in the production of the cellulose acylate film, generally includes: a method of blowing a hot air from a surface side of the metal support (dram or belt), that is to say, from the surface of a web provided on the metal support; a method of blowing a hot air from a back side of the dram or belt; a back-side liquid heat transfer method in which a temperature-modulated liquid is brought into contact with the back side opposite to the dope-casting side of the dram or belt, thereby heating the dram or belt through heat transfer to control a surface temperature; and the like. Among these, the back-side liquid heat transfer method is preferred. The surface temperature of the metal support before casting is conducted is not particularly limited as long as it is not higher than the boiling point of a solvent which is used for a dope. However, in order to accelerate drying or to make the dope lose fluidity on the metal support, the surface temperature is preferably set to a temperature which is lower by 1 to 10° C. than the boiling point of the solvent having the lowest boiling point among the solvents to be used for the dope. However, this shall not apply in the case where the casting dope is cooled and then peeled off without drying.

The adjustment of the cellulose acylate film thickness may be achieved by adjusting a concentration of the solid contained in the dope, a slit space of the die nozzle, an extrusion pressure from a die, a speed of the metal support, or the like, so as to be a desired thickness.

The thus-obtained cellulose acylate film is preferably wound at the degree of from 100 to 10,000 m, more preferably from 500 to 7,000 m, and still more preferably from 1,000 to 6,000 m, in length per roll. At the time of winding, at least one end thereof is preferably subjected to knurling. The width of knurling is preferably from 3 mm to 50 mm and more preferably from 5 mm to 30 mm. The height thereof is preferably from 0.5 µm to 500 µm and more preferably from 1 µm to 200 µm. This may be either one-way press or two-way press.

The cellulose acylate film is suitable for use in a large screen liquid crystal display. When the film is used as an optical compensation film for a large screen liquid crystal display, molding the film so as to be, for example, 1,470 mm or more in width is preferred. Further, the aspect of the polarizing plate protective film of the present invention includes a film piece that is cut to a size capable of being mounted as it is in a liquid crystal display, as well as a film that is manufactured in a long shape by continuous production and wound in a roll shape. The polarizing plate protective film of the latter aspect is stored or conveyed as it is, and is used by cutting to a desired size when the film is mounted in a liquid crystal display, or when the film and a polarizer or the like are stuck together in practice. Alternatively, the polarizing plate protective film is used by cutting to a desired size when the film is mounted in a liquid crystal display in practice after sticking the film in a long shape as it is with a polarizer composed of a polyvinyl alcohol film or the like manufactured similarly in a long shape. As an aspect of the optical compensation film which is wound in a roll shape, an aspect of a film which is wound in a roll shape and has a roll length of 2,500 m or more, is exemplified.

<<Functional Layer>>

In the optical film of the present invention, any of functional layers for different purposes may be optionally disposed on the cellulose acylate film.

Examples of the functional layer include a hard coat layer, an antireflection layer, a light scattering layer, an antifouling layer, an antistatic layer, and the like. These layers providing a plurality of functions may be combined by one layer.

As an example, the hard coat layer is a layer for imparting hardness or scratch resistance to the optical film of the present invention. It is possible to form a hard coat layer exhibiting high adhesive property with respect to the cellulose acylate film in cooperation with the compound represented by any of formula (I), (II) or (III), for example, by applying a coating composition on the cellulose acylate film and curing it. Filler and additive may be added to the hard coat layer, to thereby make the hard coat layer itself have additional mechanical, electrical or optical physical properties or chemical properties, such as water repellency or oil repellency. The thickness of the hard coat layer is preferably 0.1 to 6 μm, more preferably from 3 to 6 μm. Having such a thin hard coat layer of which the thickness falls within the range, the optical film can have improved physical properties in point of brittleness reduction and curling prevention and can attain other advantages of weight saving and production cost cutting.

Preferably, the hard coat layer is formed by curing a curable composition. Preferably, the curable composition is prepared as a liquid coating composition. One example of the coating composition contains a monomer or oligomer for matrix formation binder, other polymer, and an organic solvent. Curing the coating composition applied to the substrate film forms the intended hard coat layer. The curing reaction includes crosslinking or polymerization.

(Monomer or Oligomer for Matrix Formation Binder)

Examples of the monomer or oligomer for matrix formation binder usable in the present invention include ionizing radiation-curable polyfunctional monomers and polyfunctional oligomers. The polyfunctional monomers and the polyfunctional oligomers are preferably crosslinkable or polymerizable ones. The functional group in the ionizing radiation-curable polyfunctional monomers and polyfunctional oligomers is preferably one polymerizable through exposure to light, electron beam or radiation; and above all, especially preferred is a photopolymerizing functional group.

Examples of the photopolymerizing functional group include an unsaturated polymerizing functional group, such as a (meth)acryloyl group, a vinyl group, a styryl group, and an allyl group; a ring-opening polymerizing functional group, such as those in epoxy compounds. Above all, preferred is a (meth)acryloyl group.

Specific examples of the photopolymerizing polyfunctional monomer having a photopolymerizing functional group include: (meth)acrylic diesters of alkylene glycols, such as neopentylglycol acrylate, 1,6-hexanediol(meth) acrylate, and propyleneglycol di(meth)acrylate; (meth) acrylic diesters of polyoxyalkyleneglycols, such as triethyleneglycol di(meth)acrylate, dipropyleneglycol di(meth) acrylate, polyethyleneglycol di(meth)acrylate, and polypropyleneglycol di(meth)acrylate; (meth)acrylic diesters of polyvalent alcohols, such as pentaerythritol di(meth)acrylate; (meth)acrylic diesters of ethylene oxide or propylene oxide adducts, such as 2,2-bis{4-(acryloxy.diethoxy)phenyl}propane, and 2,2-bis{4-(acryloxy.polypropoxy)phenyl}propane.

Further, urethane(meth)acrylates, polyester(meth)acrylates, isocyanuric(meth)acrylates, and epoxy(meth)acrylates are also preferred, for use as the photopolymerizing polyfunctional monomer.

Of the above, more preferred are esters of polyvalent alcohols and (meth)acrylic acids, and even more preferred are polyfunctional monomers having at least three (meth) acryloyl groups in one molecule.

Specific examples thereof include (di)pentaerythritol tri (meth)acrylate, (di)pentaerythritol tetra(meth)acrylate, (di) pentaerythritol penta(meth)acrylate, (di)pentaerythritol hexa (meth)acrylate, tripentaerythritol triacrylate, tripentaerythritol hexaacrylate, trimethylolpropane tri(meth) acrylate, trimethylolethane tri(meth)acrylate, ditrimethylolpropane tetra(meth)acrylate, EO-modified trimethylolpropane tri(meth)acrylate, PO-modified trimethylolpropane tri (meth)acrylate, EO-modified phosphoric acid tri(meth) acrylate, 1,2,4-cyclohexane tetra(meth)acrylate, pentaglycerol triacrylate, 1,2,3-cyclohexane tetramethacrylate, polyester polyacrylate, and caprolactone-modified tris (acryloxyethyl)isocyanurate.

In this description, "(meth)acrylate", "(meth)acrylic acid" and "(meth)acryloyl" mean "acrylate or methacrylate", "acrylic acid or methacrylic acid" and "acryloyl or methacryloyl", respectively.

Further, examples include resins having at least 3 (meth) acryloyl groups, for example, polyester resins having a relatively low molecular weight, as well as polyether resins, acrylic resins, epoxy resins, urethane resins, alkyd resins, spiroacetal resins, polybutadiene resins, polythiol polyene resins, oligomers or prepolymers of polyfunctional compounds, such as polyvalent alcohols.

As concrete compounds of the polyfunctional acrylate-based compounds having at least 3 (meth)acryloyl groups, referred to is the description in JP-A-2007-256844, paragraph No. [0096], and the like.

As urethane(meth)acrylates, for example, there may be mentioned urethane(meth)acrylate-based compounds obtained by reacting a hydroxy group-containing compound, such as alcohol, polyol and/or hydroxy group-containing (meth)acrylate, with an isocyanate, followed by optionally esterifying the polyurethane compound obtained through the reaction with (meth)acrylic acid.

As specific examples of those compounds, referred to is the description in JP-A-2007-256844, [0017], and the like.

Use of isocyanuric(meth)acrylates is preferred as reducing the curling of the formed film. Isocyanuric(meth)acrylates include isocyanuric diacrylates and isocyanuric triacrylates; and as examples of those compounds, referred to is the description in JP-A-2007-256844, [0018] to [0021], and the like.

An epoxy-based compound may further be used in the hard coat layer, for reducing the shrinkage of the layer through curing. As the epoxy group-having monomers for constituting the epoxy compound, usable are monomers having at least 2 epoxy groups in one molecule. Examples of those monomers include epoxy-based monomers described in JP-A-2004-264563, JP-A-2004-264564, JP-A-2005-37737, JP-A-2005-37738, JP-A-2005-140862, JP-A-2005-140863, and JP-A-2002-322430. Also preferred is use of compounds having both epoxy and acrylic functional groups, such as glycidyl(meth)acrylate.

(Polymer Compound)

The hard coat layer may contain a polymer compound. Adding a polymer compound to the layer is preferred, as capable of reducing the curing shrinkage of the layer and capable of facilitating the viscosity control of the coating liquid that takes an interest in the dispersion stability (coagulability) of resin particles. Other advantages of the polymer compound are that the polarity of the solidified matter in the drying step may be controlled to change the coagulation behavior of resin particles and that the drying unevenness in the drying step can be reduced.

The polymer compound is already in the form of a polymer when it is added to the coating liquid. As the polymer compound of the type, preferred for use are, for example, cellulose esters (e.g., cellulose triacetate, cellulose diacetate, cellulose propionate, cellulose acetate propionate, cellulose acetate butyrate, and cellulose nitrate); and resins, such as urethanes, polyesters, (meth)acrylates (e.g., methyl methacrylate/methyl (meth)acrylate copolymer, methyl methacrylate/ethyl (meth)acrylate copolymer, methyl methacrylate/butyl (meth)acrylate copolymer, methyl methacrylate/styrene copolymer, methyl methacrylate/(meth)acrylic acid copolymer, and poly(methyl methacrylate)); and polystyrenes.

(Curable Composition)

One example of the curable composition usable for forming the hard coat layer is a curable composition containing a (meth)acrylate-based compound. Preferably, the curable composition contains a photoradical polymerization initiator or a thermal radical polymerization initiator, along with the (meth)acrylate-based compound, and if desired, may further contain a filler, a coating aid, and any of other additives. The curable composition may be cured through polymerization to be attained by exposure to ionizing radiation or to heat, in the presence of the photoradical polymerization initiator or the thermal radical polymerization initiator. Ionizing radiation curing and thermal curing may be combined. As the photoradical and thermal radical polymerization initiators, usable are commercial products, which are described in, for example, "Newest UV Curing Technology", p. 159 (issued by Kazuhiro Takausu, published by Technical Information Society of Japan, 1991), and Ciba Specialty Chemicals' catalogues.

Another example of the curable composition that can be used in forming the hard coat layer is a curable composition containing an epoxy-based compound. Preferably, the curable composition of the type contains an optical acid generator capable of generating a cation by the action of light applied thereto, along with the epoxy-based compound therein, and may optionally contain a filler, a coating aid, and any of other additives. The curable composition may be cured through polymerization to be attained by exposure to light, in the presence of an optical acid generator. Examples of the optical acid generator include ionic compounds, such as triarylsulfonium salts, diaryliodonium salts; and nonionic compounds, such as sulfonic acid nitrobenzyl ester. Various types of any optical acid generators, such as the compounds described in "Imaging Organic Material" (edited by Organic Electronics Material Society of Japan, published by Bunshin Publishing, 1997).

A (meth)acrylate-based compound and an epoxy-based compound may be combined for use. In such a case, preferably, a photoradical polymerization initiator or a thermal radical polymerization initiator is combined with an optical cationic polymerization initiator, as the polymerization initiator.

The curable composition which is particularly suitable for the formation of the hard coat layer is a composition containing a (meth)acrylate-based compound, as used in Examples to be described below.

The curable composition is preferably prepared as a coating liquid. The coating liquid can be prepared, by dissolving and/or dispersing the above-mentioned ingredients in an organic solvent.

(Property of hard coat layer)

The hard coat layer formed on the cellulose acylate film of the optical film of the present invention has high adhesive property with respect to the cellulose acylate film. In particular, in the hard coat layer formed from the preferable curable composition on the cellulose acylate film containing the compound represented by any of formula (I) to (III), the curable composition, together with the compound represented by any of formula (I) to (III), can be formed with higher adhesive property with respect to the cellulose acylate film. Thus, the optical film of the present invention having the hard coat layer and the cellulose acylate film can maintain adhesive property of the hard coat layer with respect to the cellulose acylate film even under the irradiation to light, which results in excellent light durability.

It is preferable that the hard coat layer is excellent in abrasion resistance. Concretely, when the layer is tested in a pencil hardness test (JIS 56006) that is an index of abrasion resistance, the layer preferably attains 3H or harder.

[Polarizing Plate]

The polarizing plate of the present invention has at least a polarizer and the optical film of the present invention. The polarizing plate for use in the present invention preferably has a polarizer and the optical film of the present invention provided on one side or both sides of the polarizer. Examples of the polarizer include an iodine-based polarizer, a dye-based polarizer using a dichroic dye, and a polyene-based polarizer. Ordinarily the iodine-based polarizer and the dye-based polarizer may be produced, with using a polyvinyl alcohol-based film. When the optical film of the present invention is used as a polarizing plate protective film, the production method of the polarizing plate is not particularly limited and may be produced in accordance with an ordinary manner. For example, there is a method of subjecting the cellulose acylate film of the optical film of the present invention to an alkali treatment, and besides preparing a polarizer by immersing a polyvinyl alcohol film in an iodine solution and stretching the film, and then sticking the optical film and both sides of the thus-treated polarizer together with a completely-saponified polyvinyl alcohol solution. In place of the alkali treatment, an easy adhesion processing as described in JP-A-6-94915 and JP-A-6-118232 may be used. Examples of the adhesive that is used for sticking the processed surface of the cellulose acylate film and both sides of the polarizer together include polyvinyl alcohol-based adhesives, such as polyvinyl alcohol, and polyvinyl butyral, and vinyl-based latexes derived from, such as butyl acrylate.

The optical film of the present invention and the polarizer are preferably stuck together such that a transmission axis of the polarizer and a slow axis of the optical film of the present invention are substantially bisected at right angles. It is preferable that a transmission axis of the polarizer and a slow axis of the optical film of the present invention in the liquid crystal display are stuck together so as to be substantially bisected at a right angle each other. Herein, the expression "substantially bisected at right angle" means that the direction of principal refractive index nx of the optical film of the present invention and the direction of the transmission axis of the polarizer are crossed at the angle of 90°±10°, and they are crossed preferably at the angle of 90°±5° and more preferably at the angle of 90°±1°. Setting the angle to the above range enables further reduction in light leakage under the condition of polarizing plate cross nicol. The measurement of the slow axis can be performed by various known methods and can be performed, for example, using a birefringence meter (KOBRA DH, trade name, manufactured by Oji Scientific Instruments).

The aspect of the polarizing plate of the present invention includes a film piece that is cut to a size capable of being mounted as it is in a liquid crystal display, as well as a film that is manufactured in a long shape by continuous production and wound in a roll shape (for example, an aspect having the roll length of 2,500 m or longer and an aspect having the roll length of 3,900 m or longer). When intended for the large-screen liquid crystal display, the width of the polarizing plate is preferably set to 1,470 mm or longer. The specific configuration of the polarizing plate of the present invention is not particularly limited, and any configuration may be used. For example, the configuration shown in FIG. 6 of JP-A-2008-262161 may be used.

[Liquid Crystal Display]

The liquid crystal display of the present invention has at least a liquid crystal cell and the polarizing plate of the present invention. In the liquid crystal display of the present invention, in the case where the liquid crystal display has the liquid crystal cell, a first polarizing plate, and a second polarizing plate, which are described below, the liquid crystal display is preferably an IPS, OCB, or VA mode in which at least either of the first or second polarizing plate is the polarizing plate of the present invention.

The liquid crystal display of the present invention preferably has a liquid crystal cell, and a polarizing plate which is layered on the respective side of the liquid crystal cell and equipped with an optical film on the surface of the side opposite to the liquid crystal cell side. In other words, it is preferable that the liquid crystal display of the present invention has the first polarizing plate, the liquid crystal cell, and the second polarizing plate, and is equipped with the optical film of the present invention on the surface opposite to the polarizing plate surface sandwiched between the respective polarizing plate and the liquid crystal cell. The liquid crystal display having such a configuration is excellent in suppression of display unevenness and exerts high display performance.

In addition, the liquid crystal display of the present invention preferably has the optical film, particularly the cellulose acylate film, in which the polarizing plate disposed on the visual recognition side has a hard coat layer on the surface of the optical film on the visual recognition side. The liquid crystal display having such a configuration exerts excellent excoriation resistance and light resistance in addition to high display performance excellent in suppression of display unevenness.

Figure 2:
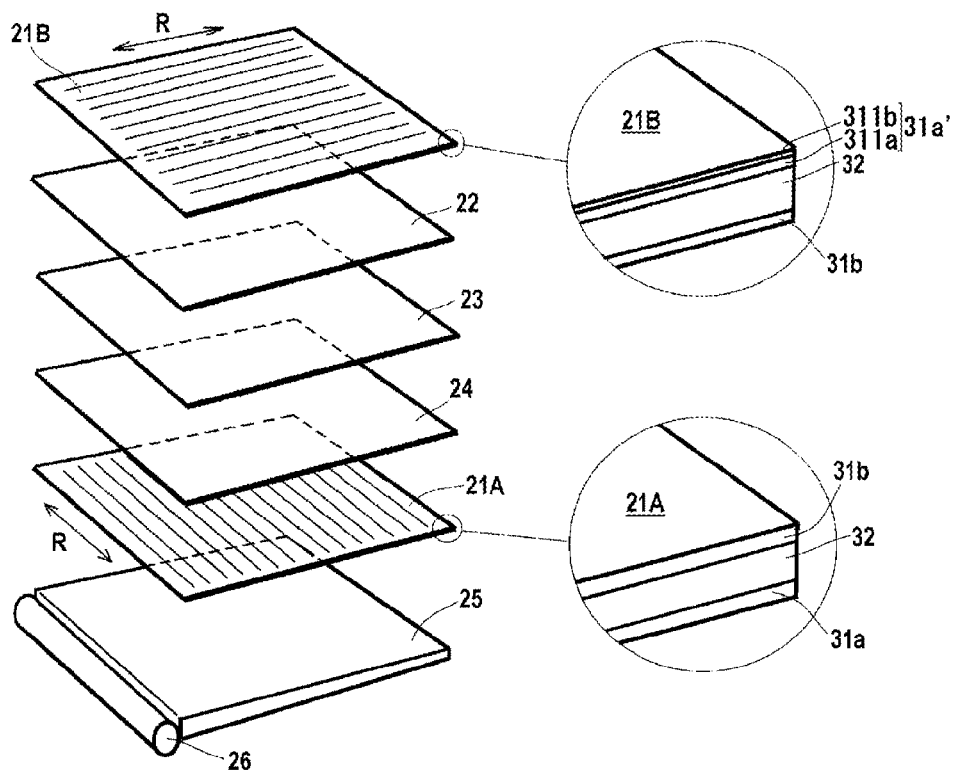
FIG. 2 is an example diagrammatically showing another internal structure of the liquid crystal display of the present invention.

As the liquid crystal display of the present invention, an internal configuration of a typical liquid crystal display is shown in FIG. 1 and FIG. 2. In FIG. 1, a liquid crystal display having polarizing plates 21A and 21B in which optical films 31a and 31b of the present invention composed of a cellulose acylate film are disposed on both surfaces of a polarizer 32 is illustrated. In addition, in FIG. 2, a liquid crystal display equipped with an optical film 31a' in which a polarizing plate 21B disposed on the visual recognition side has a hard coat layer 311b on the surface on the visual recognition side of the polarizer 32 via a cellulose acylate film 311a is illustrated.

The configuration of an example of the liquid crystal display of the present invention is illustrated in FIG. 1 and FIG. 2, but the specific configuration of the liquid crystal display of the present invention is not particularly limited, and any configuration can be adopted. Further, the configuration shown in FIG. 2 of JP-A-2008-262161 may be preferably used.

The present invention will be described in more detail based on the following examples, but the invention is not intended to be limited thereto.

EXAMPLES

Example 1

In the following manner, the optical film was obtained.
1. Preparation of Optical Film No. 101
(Preparation of Cellulose Acylate Solution 1-1)
The following composition was poured into a mixing tank, and each of components was dissolved by stirring, to prepare a cellulose acylate solution 1-1.

Composition of Cellulose Acylate Solution 1-1

| | |
|---|---|
| Cellulose acetate (acetyl substitution degree 2.87, degree of polymerization 370) | 100.0 parts by mass |
| Hydrophobidizing agent 1 (phthalic acid/ethanediol polycondensation the terminal is acetyl ester group, the average molecular weight of 800) | 10.0 parts by mass |
| Methylene chloride (first solvent) | 389.8 parts by mass |
| Methanol (second solvent) | 58.2 parts by mass |

(Preparation of Matting Agent Solution 1-2)
The following composition was poured into a dispersing machine, and each of components was dissolved by stirring, to prepare a matting agent solution 1-2.

Composition of Matting Agent Solution 1-2

| | |
|---|---|
| Silica particles having an average particle size of 20 nm (AEROSIL R972, manufactured by Nippon Aerosil Co., Ltd) | 2.0 parts by mass |
| Methylene chloride (first solvent) | 75.5 parts by mass |
| Methanol (second solvent) | 11.3 parts by mass |
| The cellulose acylate solution 1-1 | 0.9 parts by mass |

(Preparation of Adhesiveness-Improving Agent Solution 1-3)
The following composition was poured into a mixing tank, followed by dissolving the ingredients by stirring while heating, to prepare an adhesiveness-improving agent solution 1-3.

Composition of Adhesiveness-Improving Agent Solution 1-3

| | |
|---|---|
| Barbituric acid compound (BA-1) | 20.0 parts by mass |
| Exemplified compound (A-1) | 1.0 parts by mass |
| Methylene chloride (first solvent) | 73.5 parts by mass |
| Methanol (second solvent) | 6.4 parts by mass |

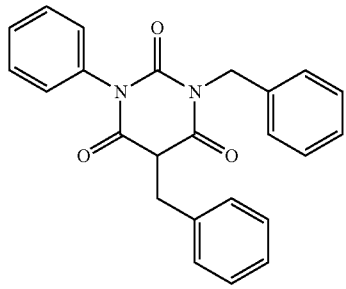

BA-1

(Preparation of Ultraviolet Absorber Solution 1-4)

The following composition was poured into a mixing tank, followed by dissolving the ingredients by stirring while heating, to prepare an ultraviolet absorber solution 1-4.

Composition of Ultraviolet Absorber Solution 1-4

| | |
|---|---|
| Ultraviolet absorber (UV-1) | 10.0 parts by mass |
| Methylene chloride (first solvent) | 78.5 parts by mass |
| Methanol (second solvent) | 11.7 parts by mass |

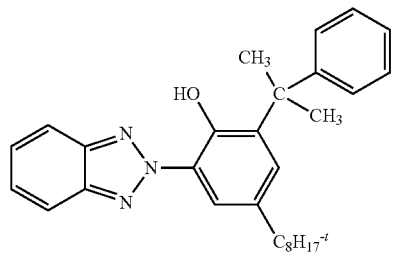

UV-1

<Casting>

1.3 parts by mass of the matting agent solution 1-2, 3.3 parts by mass of the adhesiveness-improving agent solution 1-3, and 4.0 parts by mass of the ultraviolet absorber solution 1-4 were each filtered and then mixed by using an in-line mixer, and 91.4 parts by mass of the cellulose acylate solution 1-1 was added thereto, and the mixture was mixed by using an in-line mixer. A band casting device was used to cast the thus-prepared dope on a casting support made of stainless steel (support temperature 22° C.). The film was peeled off in a state where the amount of the remaining solvent in the dope was about 20% by mass, followed by drying while being stretched by 1.10 times (10%) at a temperature of 120° C. in the width direction, in a state where the amount of the remaining solvent was 5% by mass to 10% by mass while gripping both ends of the film in the width direction with a tenter. After that, the film was further dried by letting it transport between rolls of the heat treatment apparatus, to prepare the optical film No. 101. The width and thickness of the thus-obtained optical film was 25 μm and 1,480 μm, respectively.

2. Preparation of Optical Films Nos. 102 to 113 and Nos. c01 to c03

The optical films of Nos. 102 to 112 of the present invention and the optical films Nos. c01 to c03 for comparison were produced in the same manner as the optical film of No. 101, except that the kind and the addition amount of exemplified compound to be added, and the film thickness were changed to those shown in Table 2.

The thus-prepared optical films were utilized as polarizing plate protective film as shown below, respectively.

3. Preparation of Optical Films with Hard Coat Layers

Ingredients each having the composition, as shown in Table 1 were mixed, followed by filtrating with a polypropylene filter with pore size 30 nm. Thus, each of coating liquids 1 to 6 for each hard coat layer was prepared.

TABLE 1

| Hard coat layer No. | Monomer 1 | Monomer 2 | Monomer 1/ Monomer 2 blending ratio (mass) | Monomers 1, 2 total addition amount | Photopolymerization initiator Kind | Addition amount[1] | Solvent 1 | Solvent 2 | Solvent 1/ Solvent 2 blending ratio (volume) |
|---|---|---|---|---|---|---|---|---|---|
| 1 | pentaerythrityl triacrylate | pentaerythrityl tetraacrylate | 3/2 | 53.5 | Irg 127 | 1.5 | ethyl acetate | — | — |
| 2 | pentaerythrityl triacrylate | pentaerythrityl tetraacrylate | 3/2 | 53.5 | Irg 127 | 1.5 | ethyl acetate | methyl ethyl ketone | 1/1 |
| 3 | pentaerythrityl triacrylate | pentaerythrityl tetraacrylate | 3/2 | 53.5 | Irg 127 | 1.5 | toluene | methyl isobutyl ketone | 9/1 |
| 4 | dipentaerythrityl hexaacrylate | — | — | 53.5 | Irg 127 | 1.5 | toluene | methyl isobutyl ketone | 9/1 |
| 5 | urethane acrylate UV1700B | — | — | 53.5 | Irg 184 | 1.5 | ethanol | toluene | 7/3 |
| 6 | urethane acrylate UV1700B | — | — | 53.5 | Irg 184 | 1.5 | ethanol | acetone | 7/3 |

Note:
[1] Mass % to the entire mass of the hard coat layer formation solution including the solvent(s)

[Trade Names for Employed Materials]
(Monomer)
- UV1700B: trade name, manufactured by The Nippon Synthetic Chemical Industry Co., Ltd.

(Photopolymerization Initiator)
- Irg 127: trade name, manufactured by BASF (former Ciba Specialty Chemicals)
- Irg 184: trade name, manufactured by BASF (former Ciba Specialty Chemicals)

The coating liquid 1 for the hard coat layer No. 1 shown in Table 1 was coated on the air side surface of each of the above-prepared optical films, under the condition of transportation velocity set at 30 m/minute, in accordance with a microgravure process. After drying at 60° C. for 150 seconds, the coated layer was exposed to ultraviolet ray with illuminance of 400 mW/cm$^2$ and 150 mJ/cm$^2$, using an air-cooled metal halide lamp (manufactured by EYE GRAPHICS) at 160 W/cm, while conducting nitrogen purge (oxygen concentration 0.5% or less), thereby for curing the coated layer. Thus, a hard coat layer (6 μm thickness) was formed.

In this manner, the hard coat layer was formed on the air side surface of each of the optical films, to prepare optical films with the hard coat layers.

4. Preparation of Polarizing Plate

The optical films with the hard coat layers produced above were soaked in 2.3 mol/L sodium hydroxide aqueous solution at 55° C. for 3 minutes. The resultant films were then washed in a water-washing bath tank at room temperature and neutralized with 0.05 mol/L sulfuric acid at 30° C. The films were, again, washed in a water-washing bath tank at room temperature, followed by drying by warm air at 100° C. Thus, the saponification treatment was conducted.

Iodine was adsorbed onto a stretched polyvinyl alcohol film, to prepare a polarizer.

Each of the saponified optical films with the hard coat layers was stuck on one side of the polarizer, using a polyvinyl alcohol-based adhesive. Herein, the polarizer was stuck together with the surface of the side of the optical film on which the hard coat layer was not coated, that is to say, a surface of the surface layer on the support side of the optical film. A cellulose triacetate film (FUJITAC TD 80UF, trade name, manufactured by FUJIFILM Corporation) which is a commercially-available optical film was subjected to the saponification in the same manner as the above. The commercially-available cellulose acetate film after saponification was stuck, using a polyvinyl alcohol-based adhesive, on the side of the polarizer opposite to the side at which each of the optical films with the hard coat layers had been stuck.

At this time, a transmission axis of the polarizer and a slow axis of each of the optical films with hard coat layers were arranged so as to be at right angles to one another. Further, a transmission axis of the polarizer and a slow axis of the commercially-available cellulose acetate film were also arranged so as to be at right angles to one another.

In this manner, polarizing plates Nos. 101 to 113 of the present invention and polarizing plates Nos. c01 to c03 for comparison, all of which are polarizing plates with the hard coat layer, were each prepared.

Light-resistant adhesiveness of each of the thus-prepared polarizing plates and thermal stability of the hydroxyamine compounds which are the compounds represented by any of formulas (I) to (III) for use in the present invention, were evaluated.

(Evaluation of Light-Resistant Adhesiveness)

Firstly, each of the above-prepared optical films with the hard coat layers (protective films for polarizing plates) was exposed to light for 100 hours under the conditions of 60° C. and 50% relative humidity, using Super XENON weather meter SX75 (trade name) manufactured by Suga Test Instruments Co., Ltd.

Next, each of the optical films with the hard coat layers was subjected to humidity conditioning for 2 hours under the conditions of temperature: 25° C. and relative humidity: 60%. On the surface of the side having the hard coat layer, 11 incisions in a longitudinal direction and 11 incisions in a transverse direction were made grid-wise using a cutter knife, to incise the total of 100-square grids. Then, a polyester adhesive tape (No. 31B) manufactured by Nitto Denko Corporation was put on the surface. After the lapse of time 30 minutes, the tape was rapidly peeled off in a vertical direction, to count the number of peeled grids.

This evaluation was repeated three times, to measure an average value of the number of peeled grids. Evaluation was conducted in accordance with the following four-level criterion.

The ranks A and B of the evaluation criterion are in an acceptable range.

Evaluation Criterion
- A: Peeled grids are 7 or less with respect to 100 grids
- B: Peeled grids are from 8 to 15 with respect to 100 grids
- C: Peeled grids are from 16 to 30 with respect to 100 grids
- D: Peeled grids are 31 or more with respect to 100 grids (Evaluation of Thermal Stability of Compound)

The rate of mass decrease at the time when 5 mg of the hydroxyamine compound was subjected to temperature rising at the rate of temperature rising: 20° C./min, and then held at 140° C. for 60 minutes was measured, using a differential thermogravimetric simultaneous-measuring device EXSTAR TG/DTA6000 (trade name) manufactured by Yamato Scientific. Then, evaluation was conducted in accordance with the following four-level criterion.

The ranks A and B of the evaluation criterion are in an acceptable range.
- A: The rate of mass decrease is less than 1%
- B: The rate of mass decrease is 1% or more and less than 5%
- C: The rate of mass decrease is 5% or more and less than 10%
- D: The rate of mass decrease is 10% or more The results are shown together in Table 2.

TABLE 2

| Optical film No. | Hydroxyamine compound | | Barbituric acid compound | | Film thickness [μm] | Light-resistance adhesiveness | Thermal stability of hydroxylamine compound | Remarks |
| --- | --- | --- | --- | --- | --- | --- | --- | --- |
| | Compound No. | Addition amount[1] | Compound No. | Addition amount[1] | | | | |
| 101 | A-1 | 0.2 | BA-1 | 4 | 25 | A | A | This invention |
| 102 | A-1 | 0.06 | BA-1 | 4 | 25 | B | A | This invention |

TABLE 2-continued

| Optical film No. | Hydroxyamine compound Compound No. | Addition amount[1] | Barbituric acid compound Compound No. | Addition amount[1] | Film thickness [μm] | Light-resistance adhesiveness | Thermal stability of hydroxylamine compound | Remarks |
|---|---|---|---|---|---|---|---|---|
| 103 | A-1 | 0.4 | BA-1 | 4 | 25 | A | A | This invention |
| 104 | A-1 | 0.2 | BA-1 | 4 | 40 | A | A | This invention |
| 105 | A-1 | 0.2 | BA-1 | 4 | 60 | A | A | This invention |
| 106 | A-1 | 0.2 | BA-1 | 4 | 80 | A | A | This invention |
| 107 | A-2 | 0.2 | BA-1 | 4 | 25 | A | A | This invention |
| 108 | A-3 | 0.2 | BA-1 | 4 | 25 | A | A | This invention |
| 109 | A-4 | 0.2 | BA-1 | 4 | 25 | B | B | This invention |
| 110 | A-14 | 0.2 | BA-1 | 4 | 25 | B | A | This invention |
| 111 | A-1 and A-4 | A-1: 0.1 A-4: 0.1 | BA-1 | 4 | 25 | A | A | This invention |
| 112 | A-1 | 0.2 | BA-2 | 4 | 25 | A | A | This invention |
| 113 | A-14 | 0.2 | none | — | 25 | B | A | This invention |
| c01 | B-2 | 0.2 | BA-1 | 4 | 25 | C | D | Comparative example |
| c02 | B-3 | 0.2 | BA-1 | 4 | 25 | C | D | Comparative example |
| c03 | none | — | none | — | 25 | D | — | Comparative example |

Note:
[1] Parts by mass to 100 parts by mass of the resin

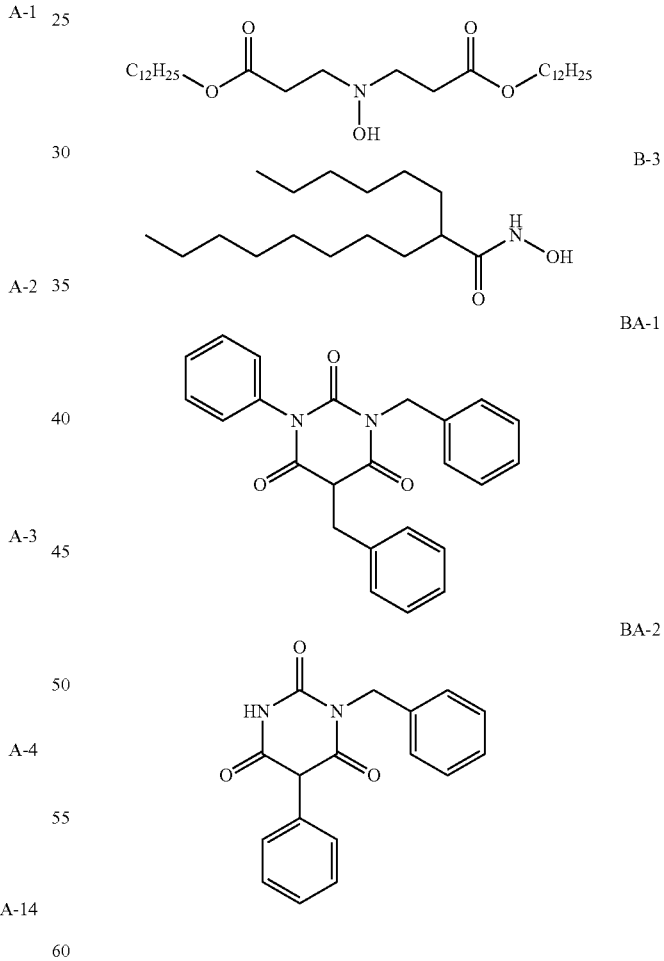

As is apparent from Table 2, all the compounds represented by any of formulas (I) to (III) for use in the present invention are excellent in thermal stability of the compound itself. Further, the protective films for polarizing plates which are optical films of the present invention which contain the compounds represented by any of formulas (I) to (III) are excellent in light-resistant adhesiveness.

In addition, from comparison with the optical film No. c03 for comparison, which does not contain the compound represented by any of formulas (I) to (III) for use in the present invention, it is understood that the compounds represented by any of formulas (I) to (III) for use in the present invention contribute largely to improvement in light-resistant adhesiveness.

Contrary to the above, in the optical film Nos. c01 and c02 for comparison, which use respectively compounds B-2 and B-3 for comparison, not in the definition but similar to the compound represented by any of formulas (I) to (III) for use in the present invention, an evaluation results which are inferior by one rank and not in an acceptable level, in terms of light-resistant adhesiveness were obtained, and thermal stability of the compound itself was poor.

Example 2

Optical films with hard coat layers which are different from those of Example 1, except that the hard coat layer in Example 1 was changed from No. 1 to one of Nos. 2 to 6 were prepared, respectively. Then, each polarizing plate was prepared and light-resistant adhesiveness thereof was evaluated in the same manner as in Example 1. As a result, it was confirmed that in any of the hard coat layers, any of the optical films and the polarizing plates of the present invention containing the compound represented by any of formulas (I) to (III) for use in the present invention, were superior to those containing compounds for comparison. The results, herein, show that a liquid crystal display which exerts such excellent performance as shown in the above can be prepared, by using the polarizing plate of the present invention.

REFERENCE SIGNS LIST 21A, 21B Polarizing plate
22 Color filter substrate
23 Liquid crystal layer (liquid crystal cell)
24 Array substrate
25 Light guide plate
26 Light source
31a, 31a', 31b Optical film (polarizing plate protective film)
311a Cellulose acylate film
311b Hard coat layer
32 Polarizer
R Polarization direction

The invention claimed is:

1. An optical film, containing a cellulose acylate, and at least one compound represented by any of formulas (I) to (III):

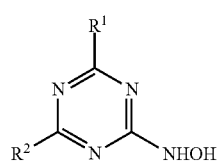

Formula (I)

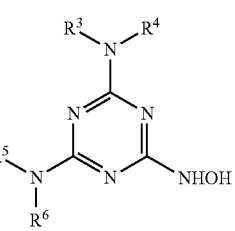

Formula (II)

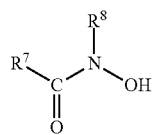

Formula (III)

wherein, $R^1$ and $R^2$ each independently represent a halogen atom, an alkyl group having 1 to 20 carbon atoms, a cycloalkyl group having 3 to 20 carbon atoms, an alkenyl group having 2 to 20 carbon atoms, an aryl group having 6 to 20 carbon atoms, a hydroxy group, a hydroxyamino group, an amino group, an alkylamino group having 1 to 20 carbon atoms, an arylamino group having 6 to 20 carbon atoms, an alkoxy group having 1 to 20 carbon atoms, an aryloxy group having 6 to 20 carbon atoms, an alkylthio group having 1 to 20 carbon atoms, or an arylthio group having 6 to 20 carbon atoms, wherein, $R^1$ and $R^2$ do not represent an amino group, an alkylamino group, or an arylamino group at the same time; $R^3$ to $R^6$ each independently represent a hydrogen atom, an alkyl group having 1 to 20 carbon atoms, a cycloalkyl group having 3 to 20 carbon atoms, an alkenyl group having 2 to 20 carbon atoms, an aryl group having 6 to 20 carbon atoms, an acyl group having 1 to 20 carbon atoms, an alkylsulfonyl group having 1 to 20 carbon atoms, an arylsulfonyl group having 6 to 20 carbon atoms, an alkylsulfinyl group having 1 to 20 carbon atoms, an arylsulfinyl group having 6 to 20 carbon atoms, a carbamoyl group having 1 to 20 carbon atoms, a sulfamoyl group having 0 to 20 carbon atoms, an alkoxycarbonyl group having 2 to 20 carbon atoms, or an aryloxycarbonyl group having 7 to 20 carbon atoms; $R^7$ represents an alkyl group having 1 to 20 carbon atoms, a cycloalkyl group having 3 to 20 carbon atoms, an alkenyl group having 2 to 20 carbon atoms, an aryl group having 6 to 20 carbon atoms, an aryloxy group having 6 to 20 carbon atoms, or a heterocyclic group having 0 to 20 carbon atoms; $R^8$ represents an alkyl group having 1 to 3 carbon atoms, a cycloalkyl group having 3 to 20 carbon atoms, an alkenyl group having 2 to 20 carbon atoms, an aryl group having 6 to 20 carbon atoms, or a heterocyclic group having 0 to 20 carbon atoms; and each of $R^1$ to $R^8$ may be further substituted with a substituent, further containing at least one compound represented by formula (BA):

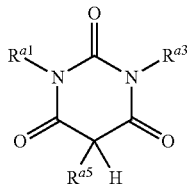

Formula (BA)

wherein, $R^{a1}$, $R^{a3}$ and $R^{a5}$ each independently represent a hydrogen atom, an alkyl group having 1 to 20 carbon atoms, a cycloalkyl group having 3 to 20 carbon atoms, an alkenyl group having 2 to 20 carbon atoms, or an aryl group having 6 to 20 carbon atoms; herein, the alkyl group, the cycloalkyl group, the alkenyl group, and the aryl group may have a substituent.

2. The optical film according to claim 1, wherein any one of $R^{a1}, R^{a3}$ and $R^{a5}$ in the compound represented by formula (BA) is an aralkyl group, or the cycloalkyl group, and the sum of ring structures which exist in $R^{a1}$, $R^{a3}$ and $R^{a5}$ is 3 or more.

3. The optical film according to claim 1, wherein the total acyl substitution degree (A) of the cellulose acylate satisfies formula:

1.5<A<3.0.

4. The optical film according to claim 1, wherein the acyl group of the cellulose acylate is an acetyl group, and the total acetyl substitution degree (B) of the cellulose acylate satisfies formula:

2.0<B<3.0.

5. The optical film according to claim 1, wherein a thickness of the optical film is from 5 μm to 80 μm.

6. A polarizing plate containing the optical film according to claim 1.

7. A liquid crystal display containing the polarizing plate according to claim 6.

* * * * *